United States Patent
Oishi et al.

(10) Patent No.: US 12,268,803 B2
(45) Date of Patent: Apr. 8, 2025

(54) BLOOD PURIFIER

(71) Applicant: Asahi Kasei Medical Co., Ltd., Tokyo (JP)

(72) Inventors: Teruhiko Oishi, Tokyo (JP); Yusuke Tokimizu, Tokyo (JP); Keitaro Matsuyama, Tokyo (JP); Naoki Morita, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 705 days.

(21) Appl. No.: 17/426,841

(22) PCT Filed: Mar. 27, 2020

(86) PCT No.: PCT/JP2020/014376
§ 371 (c)(1),
(2) Date: Jul. 29, 2021

(87) PCT Pub. No.: WO2020/203923
PCT Pub. Date: Oct. 8, 2020

(65) Prior Publication Data
US 2022/0111133 A1    Apr. 14, 2022

(30) Foreign Application Priority Data

Mar. 29, 2019  (JP) .................................. 2019-068818
Jan. 15, 2020  (JP) .................................. 2020-004699

(51) Int. Cl.
*A61M 1/36*     (2006.01)
*B01J 20/06*    (2006.01)
(Continued)

(52) U.S. Cl.
CPC .......... *A61M 1/3633* (2013.01); *A61M 1/361* (2014.02); *B01J 20/06* (2013.01);
(Continued)

(58) Field of Classification Search
CPC .. A61M 1/3633; A61M 1/361; A61M 1/3639; A61M 1/3679; A61M 1/02;
(Continued)

(56) References Cited

U.S. PATENT DOCUMENTS

2002/0060180 A1    5/2002  Sugisaki
2003/0125656 A1    7/2003  Davankov et al.
(Continued)

FOREIGN PATENT DOCUMENTS

CN    1543374      11/2004
CN    101151056    3/2008
(Continued)

OTHER PUBLICATIONS

Supplementary European Search Report issued in European Patent Application No. 20785112.2 mailed on Apr. 21, 2022.
(Continued)

*Primary Examiner* — Akash K Varma
(74) *Attorney, Agent, or Firm* — GREENBLUM & BERNSTEIN, P.L.C.

(57) ABSTRACT

A blood purifier includes a porous molded body; exhibits an excellent blood compatibility wherein platelet adherence is inhibited and exhibits a good cytokine adsorption capacity and a low pressure loss before and after blood treatment; and can be safely used. A blood purifier includes a main vessel and a porous molded body housed in the main vessel. The porous molded body contains a hydrophobic polymer and a hydrophilic polymer. The amount of low-melting-point water per 1 g of dry weight of the porous molded body is 0.12 g to 2.00 g. The contact change ratio for the porous molded body is 0% to 0.2%. The ratio L/D is 1.00 to 2.30 where, for the region taken up by the porous molded body in the main vessel, L is the length in the flow direction and
(Continued)

D is the circle-equivalent diameter of the cross section in the direction perpendicular to the flow direction.

12 Claims, 7 Drawing Sheets

(51) Int. Cl.
   *B01J 20/26* (2006.01)
   *B01J 20/28* (2006.01)
   *B01J 20/285* (2006.01)
   *B01J 20/32* (2006.01)

(52) U.S. Cl.
   CPC ........... *B01J 20/261* (2013.01); *B01J 20/262* (2013.01); *B01J 20/28016* (2013.01); *B01J 20/28071* (2013.01); *B01J 20/28085* (2013.01); *B01J 20/285* (2013.01); *B01J 20/327* (2013.01)

(58) Field of Classification Search
   CPC ........... A61M 1/36; A61M 1/14; A61M 1/16; A61M 1/34; A61M 1/36165; A61M 1/0213; A61M 2205/05; B01J 20/06; B01J 20/261; B01J 20/262; B01J 20/28016; B01J 20/28071; B01J 20/28085; B01J 20/285; B01J 20/327; B01J 20/264; B01J 20/28004; B01J 20/28069; B01J 20/28; B01J 20/30; B01J 20/321; B01J 20/3212; B01J 20/3214; B01J 20/3276; B01J 20/3293; B01J 20/08; B01J 20/10; B01J 20/26; B01J 20/32; B01J 20/28011; B01J 20/2803; B01J 20/28042; B01J 2220/44; B01J 2220/46; B01D 39/1653; B01D 39/16; B01D 2239/0421; B01D 2239/0428; B01D 2239/1208; B01D 2239/1216; B01D 24/02; B01D 71/28; B01D 71/76
   USPC ....................................................... 210/500.1
   See application file for complete search history.

(56) References Cited

U.S. PATENT DOCUMENTS

| | | |
|---|---|---|
| 2004/0178140 A1 | 9/2004 | Bell |
| 2004/0206692 A1 | 10/2004 | Oishi et al. |
| 2005/0063935 A1* | 3/2005 | Hirai .................. B01J 20/28021 210/645 |
| 2005/0145561 A1 | 7/2005 | Takai et al. |
| 2006/0137718 A1 | 6/2006 | Kin et al. |
| 2007/0128424 A1 | 6/2007 | Omori et al. |
| 2008/0245723 A1 | 10/2008 | Komura et al. |
| 2009/0275874 A1 | 11/2009 | Shimagaki et al. |
| 2015/0174312 A1 | 6/2015 | Ichi et al. |
| 2016/0263294 A1 | 9/2016 | Anzai |
| 2016/0303296 A1 | 10/2016 | Anzai et al. |
| 2017/0128636 A1 | 5/2017 | Anzai et al. |
| 2017/0173231 A1* | 6/2017 | Kiriyama ........... B01J 20/28033 |
| 2018/0162977 A1 | 6/2018 | Ushiro et al. |
| 2018/0326136 A1 | 11/2018 | Morita et al. |
| 2019/0076819 A1 | 3/2019 | Fujieda et al. |
| 2020/0171479 A1 | 6/2020 | Morita et al. |
| 2021/0008270 A1 | 1/2021 | Oishi et al. |
| 2021/0170362 A1 | 6/2021 | Tokimizu et al. |

FOREIGN PATENT DOCUMENTS

| | | |
|---|---|---|
| CN | 104258829 | 1/2015 |
| CN | 105348541 | 2/2016 |
| CN | 105992600 | 10/2016 |
| CN | 107406551 | 11/2017 |
| EP | 3777915 | 2/2021 |
| JP | 08-294531 | 11/1996 |
| JP | 2002-102335 | 4/2002 |
| JP | 2004-161954 | 6/2004 |
| JP | 2006-012791 | 1/2006 |
| JP | 2006-341240 | 12/2006 |
| JP | 2007-130194 | 5/2007 |
| JP | 2007-330840 | 12/2007 |
| JP | 2010-233999 | 10/2010 |
| JP | 4671419 | 1/2011 |
| JP | 2011-030903 | 2/2011 |
| JP | 2011-224142 | 11/2011 |
| JP | 2015-116212 | 6/2015 |
| JP | 2016-77570 | 5/2016 |
| JP | 2016-514568 | 5/2016 |
| JP | 2017-25285 | 2/2017 |
| JP | 2017-86563 | 5/2017 |
| JP | 2017-185037 | 10/2017 |
| JP | 2017-185221 | 10/2017 |
| JP | 2019-018193 | 2/2019 |
| JP | 2019-177042 | 10/2019 |
| WO | 03/055545 | 7/2003 |
| WO | 2004/006991 | 1/2004 |
| WO | 2007/018242 | 2/2007 |
| WO | 2011/125758 | 10/2011 |
| WO | 2014/165421 | 10/2014 |
| WO | 2015/093160 | 6/2015 |
| WO | 2015/098763 | 7/2015 |
| WO | 2015/125890 | 8/2015 |
| WO | 2016/013540 | 1/2016 |
| WO | 2017/082423 | 5/2017 |
| WO | 2018/212269 | 11/2018 |
| WO | 2019/189881 | 10/2019 |
| WO | 2019/189884 | 10/2019 |
| WO | 2020/009008 | 1/2020 |

OTHER PUBLICATIONS

Morita, Shigeaki et al., "Time-Resolved In Situ ATR-IR Observations of the Process of Sorption of Water into a Poly(2-methoxyethyl acrylate) Film", American Chemical Society, 2007, pp. 3750-3761.

Tsuruta, Teiji et al., "On the Role of Water Molecules in the Interface between Biological Systems and Polymers", The University of Tokyo, Jan. 19, 2010, pp. 1831-1848.

Tanaka, Masaru et al., "Thermal Characterization of Novel Polymers of Biomedical Applications", Netsu Sokutei, vol. 39, No. 4, Oct. 31, 2012, pp. 151-157.

Kobayashi, Shingo et al., "Precise synthesis technology of novel polymer containing intermediate water for medical, "The relationship between intermediate water vol. and platelet adhesion number"", New Technical Explanation Conference, Jan. 22, 2015, pp. 1-17.

Nakaoka, Ryusuke, "Biological safety assessmement required for approval examination of medical devices and its international standardization status", Documents of the Symposium 2016 of the Japanese Society for Biomaterials, Nov. 21, 2016, pp. 1-21.

International Search Report and Written Opinion of the International Searching Authority issued in International Patent Application No. PCT/JP2020/014376, dated Jun. 23, 2020, along with an English translation thereof.

International Preliminary Report on Patentability and issued in International Patent Application No. PCT/JP2020/014376, dated Sep. 28, 2021, along with an English translation thereof.

Yukihiro Yoshimoto, et.al., "Towards the Next Generation of Implantable Biomedical Devices Using Diamond-Like Carbon Coatings", Journal of The Surface Finishing Society of Japan, (2008), vol. 59, No. 6, pp. 363-370.

* cited by examiner

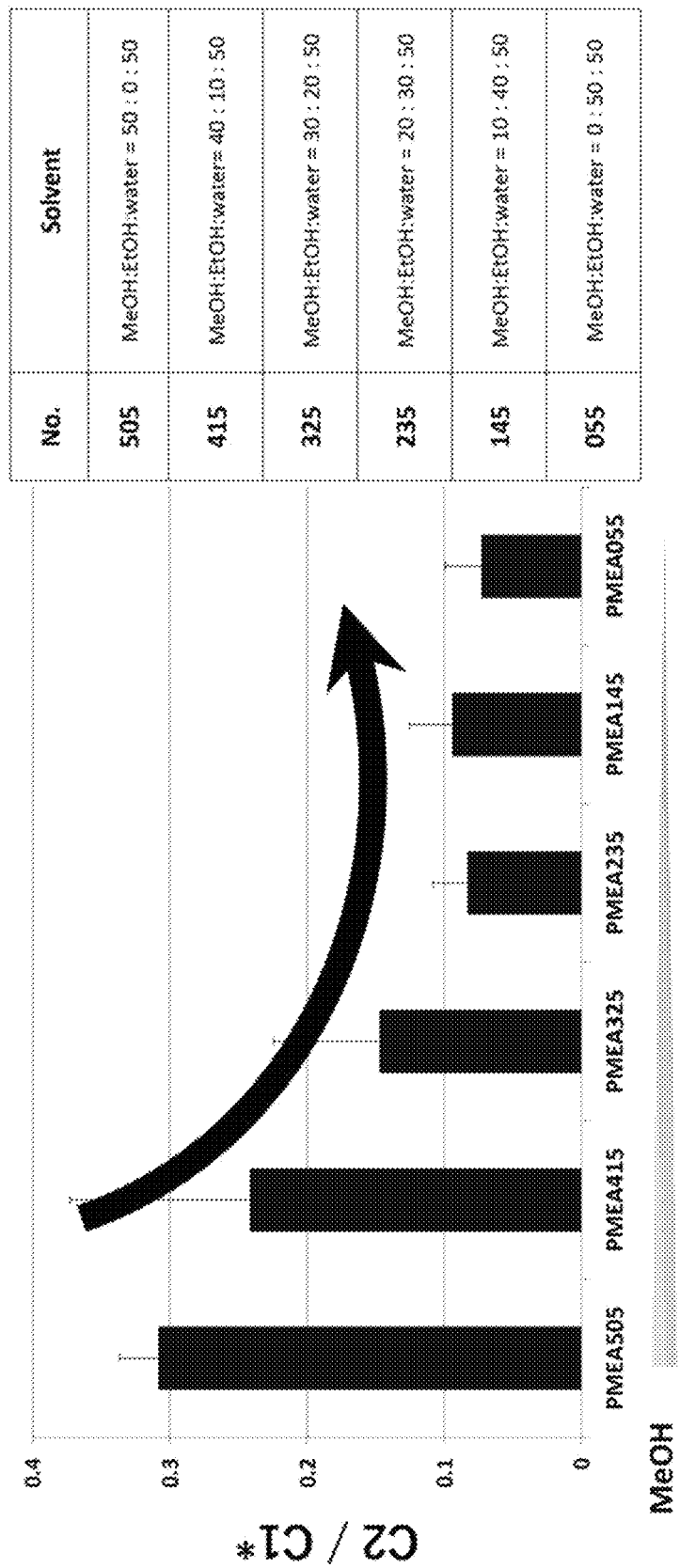

BLOOD PURIFIER

FIELD

The present invention relates to a blood purifier.

BACKGROUND

Various apheresis therapies which remove inflammatory mediators considered as causative substances, for example, cytokines and alarmins, from the blood of patients have been practiced in the treatment of ischemic diseases including sepsis. In recent years, the development of adsorption type blood purifiers for removing inflammatory mediators by adsorption has been underway as one of the apheresis therapies.

Examples of launched adsorption type blood purifiers include: Tremixin® (Toray Medical Co., Ltd.) using an adsorbent around which fiber having an endotoxin removal function is wound in roll; sepXiris® (Baxter Ltd.), an adsorption type blood purifier intended for continuous renal replacement therapy (CRRT), using hollow fiber having an alarmin (HMGB1) and cytokine (IL-6, etc.) adsorption function; and CytoSorb® (Cytosorbents Corp.) using a porous formed article of a porous polymer having a cytokine removal function.

Blood purifiers are required to have biocompatibility because the blood purifiers come into direct contact with the blood of patients. In order to impart the biocompatibility to the blood purifiers, adsorbents are coated with biocompatible polymers, typically, hydrophilic polymers.

For example, PTL 1 discloses an antithrombogenic coating material which is produced by adding a specific radical polymerization initiator to a methanol solution containing a monomer having a specific structure, and performing polymerization reaction. This antithrombogenic coating material is applied to medical equipment such as prostheses (e.g., ePTFE vascular prostheses) and catheters and can thereby impart biocompatibility thereto.

PTL 2 discloses a copolymer having a specific structure, comprising a monomeric unit having a nonionic group, a monomeric unit having a basic nitrogen-containing functional group, and a monomeric unit having a N value of 2 or less when forming a homopolymer. This copolymer can be supported on a filter, thereby providing a living body-derived fluid processing filter capable of processing a living body-derived fluid containing erythrocytes without adversely affecting erythrocytes.

PTL 3 discloses that a porous formed article as an adsorbent is coated with a cross-linked polymer material having a plurality of at least one of a zwitterionic moiety and an oligoethylene glycol moiety.

PTL 4 discloses a biocompatible polymer obtained by copolymerizing N-methacryloyloxyethyl-N,N-dimethylammonium-α-N-methylcarboxybetaine (CMB) with a polymerizable monomer having biocompatibility, represented by an alkene compound having one double bond and an organic group.

PTL 5 discloses a biocompatible polymer obtained by copolymerizing 2-methoxyethyl acrylate (MEA) with N-methacryloyloxyethyl-N,N-dimethylammonium-α-N-methylcarboxybetaine (CMB), the biocompatible polymer comprising 1 to 7% by mol of the CMB in all monomeric units.

PTL 6 discloses a biocompatible polymer obtained by copolymerizing 2-methoxyethyl acrylate (MEA) with [2-(methacryloyloxy)ethyl]dimethyl-(3-sulfopropyl)ammonium hydroxide (SPB) or [3-(methacryloylamino)propyl]dimethyl(3-sulfopropyl)ammonium hydroxide (SPBA), the biocompatible polymer comprising 1 to 7% by mol of the SBAC in all monomeric units.

PTL 7 discloses a phosphorus binder for blood processing containing a porous formed article comprising an organic polymer resin and an inorganic ion adsorbent and having a specific modal pore size range.

PTL 8 discloses a phosphorus binder for blood processing in which the surface of a porous formed article comprising an organic polymer resin and an inorganic adsorbent and having a specific modal pore size range is coated with a biocompatible polymer.

PTL 9 discloses a blood purifier having a dialysis membrane in a hollow fiber form comprising an inorganic ion adsorbent with enhanced clearance of phosphorus.

PTL 10 and PTL 11 disclose a blood purifier having a porous formed article comprising an inorganic ion adsorbent with reduced levels of metal eluates or fine particles.

PTL 12 discloses an adsorption material for removing cytokines and HMGB1 at the same time from blood by adsorption while minimizing a loss of useful proteins. This literature discloses two Examples of PES+PEG35000+hydrous cerium oxide and EVOH+PVP (K30)+hydrous zirconium oxide. However, PEG35000 and PVP (K30) are soluble in water and therefore are not suitable for hemofiltration as described in the present application.

PTL 7 to PTL 11 specify performance of removing phosphorus from blood by adsorption, but disclose nothing about favorable removal of cytokines by adsorption from blood.

PTL 12 discloses a porous formed article comprising a hydrophobic polymer, a hydrophilic polymer and a cytokine adsorbent. However, an HMGB1 adsorption rate is less than 60% and is thus not preferred because polyvinylpyrrolidone having a weight-average molecular weight of 1,100,000 or higher is not used as the hydrophilic polymer. Such an adsorption type blood purifier is expected to be utilized in the treatment of ischemic diseases as well as the case where the overproduction of inflammatory mediators is of concern, such as cardiac surgery and organ transplantation surgery.

PTL 13 discloses that phosphorus in blood is efficiently removed, without direct contact between a phosphorus binder and the blood, by circulating a dialysis composition comprising the phosphorus binder in a dialysate at the time of hemodialysis.

PTL 14 discloses a hemodialysis system in which a phosphorus binder made of a polycation polymer for removing phosphorus accumulated in blood is disposed, aside from a hemodialyzer, in an extracorporeal blood circuit.

PTL 15 discloses a porous formed article suitable for binders, which can remove phosphorus or the like by adsorption at a high speed.

CITATION LIST

Patent Literature

[PTL 1] Japanese Unexamined Patent Publication No. 2017-025285
[PTL 2] Japanese Unexamined Patent Publication No. 2017-185037
[PTL 3] Japanese Translation of PCT International Application Publication No. 2016-514568
[PTL 4] Japanese Unexamined Patent Publication No. 2007-130194
[PTL 5] International Publication No. WO 2015/098763

[PTL 6] International Publication No. WO 2015/125890
[PTL 7] International Publication No. WO 2017/082423
[PTL 8] International Publication No. WO 2018/212269
[PTL 9] Japanese Unexamined Patent Publication No. 2019-177042
[PTL 10] International Publication No. WO 2019/189881
[PTL 11] International Publication No. WO 2019/189884
[PTL 12] Japanese Unexamined Patent Publication No. 2017-86563
[PTL 13] International Publication No. WO 2011/125758
[PTL 14] Japanese Unexamined Patent Publication No. 2002-102335
[PTL 15] Japanese Patent No. 4671419

Non Patent Literature

[NPL 1] Shigeaki Morita, Masaru Tanaka and Yukihiro Ozaki, "Time-Resolved In Situ ATR-1R Observations of the Process of Sorption of Water into a Poly(2-methoxyethyl acrylate) Film", Langmuir, 2007, 23 (7), publication date (web): Mar. 3, 2007, pp. 3750-3761
[NPL 2] T. Tsuruta, J. Biomater. et al., "The roles of water molecules in the interfaces between biological systems and polymers", Sci. Polvm. Ed., 21, 2010, pp. 1827-1920

SUMMARY

Technical Problem

An object of the present invention is to provide a blood purifier having a porous formed article, which is excellent in blood compatibility that resists platelet attachment (hereinafter, simply referred to as "blood compatibility"), has favorable cytokine adsorption performance, has a low pressure loss before and after blood processing, and is safely usable.

In one embodiment, an object of the present invention is to provide a porous formed article having improved blood compatibility while maintaining the adsorbability of the porous formed article.

In one embodiment, an object of the present invention is to solve one or more problems of medical equipment having a conventional biocompatible polymer described above in PTL 1 to PTL 6, etc.

For example, when a porous formed article as an adsorbent is coated with a conventional biocompatible polymer (or a conventional biocompatible polymer is "supported" on a porous formed article as also described in the specification of the present application) as described above in PTL 1 to PTL 3, etc., adsorbability for inflammatory mediators which are hydrophobic proteins is reduced due to hydrophilized surface of the porous formed article, though the biocompatibility of the porous formed article can be improved. Hence, improvement in biocompatibility and improvement in adsorbability are considered to be in a tradeoff relationship.

Solution to Problem

The present inventors have found that a blood purifier excellent in blood compatibility is obtained by the adjustment of a low-melting point water content of a porous formed article, and successfully reduced a pressure loss of the blood purifier before and after blood processing. The present inventors have further found that: a blood purifier having favorable cytokine adsorption performance is obtained by the adjustment of a low-melting point water content of a porous formed article; and a safely usable blood purifier is obtained by the adjustment of a contact-induced change rate (also called "stirring abrasion rate") of a porous formed article. On the basis of these findings, the present invention has been completed.

An exemplary embodiment of the present invention is as follows:

A blood purifier having a body vessel and a porous formed article placed in the body vessel, wherein:
the porous formed article comprises a hydrophobic polymer and a hydrophilic polymer, has a low-melting point water content of 0.12 g or larger and 2.00 g or smaller per 1 g dry weight of the porous formed article, and has a contact-induced change rate of 0% or more and 0.2% or less;
ratio L/D of length L in the longitudinal direction to equivalent circle diameter D at a cross section in the shorter direction of a region occupied by the porous formed article in the body vessel is 1.00 or more and 2.30 or less, wherein the equivalent circle diameter D is calculated according to the following expression (1):

$$D = 2\sqrt{V/L/3.14} \qquad (1)$$

wherein V represents an apparent volume of the region occupied by the porous formed article in the body vessel; and
the blood purifier has a pressure loss of less than 13 kPa before blood processing and has a pressure loss of less than 13 kPa after blood processing when an aqueous polyvinylpyrrolidone solution having a viscosity of 3.75 mPa·s or higher and 3.85 mPa·s or lower is flowed in the blood purifier at a passing rate of 400 mL/min.

ADVANTAGEOUS OF EFFECTS OF INVENTION

The blood purifier according to the present invention is excellent in blood compatibility, has favorable cytokine adsorption performance, has a low pressure loss before and after blood processing, and is safely usable.

In a preferred embodiment, the blood purifier of the present invention is excellent in selectivity and adsorbability for cytokines and high-mobility group box 1 (HMGB1) in blood even at a high blood flow rate at the time of extracorporeal circulation treatment, and can eliminate necessary amounts of cytokines and high-mobility group box 1 (HMGB1) from the blood without affecting other components in the blood.

BRIEF DESCRIPTION OF DRAWINGS

FIG. 7 is a graph illustrating difference in the amount of PMEA coating among solvents in a PMEA coating solution.

DESCRIPTION OF EMBODIMENTS

[Blood Purifier]

Figure 1:
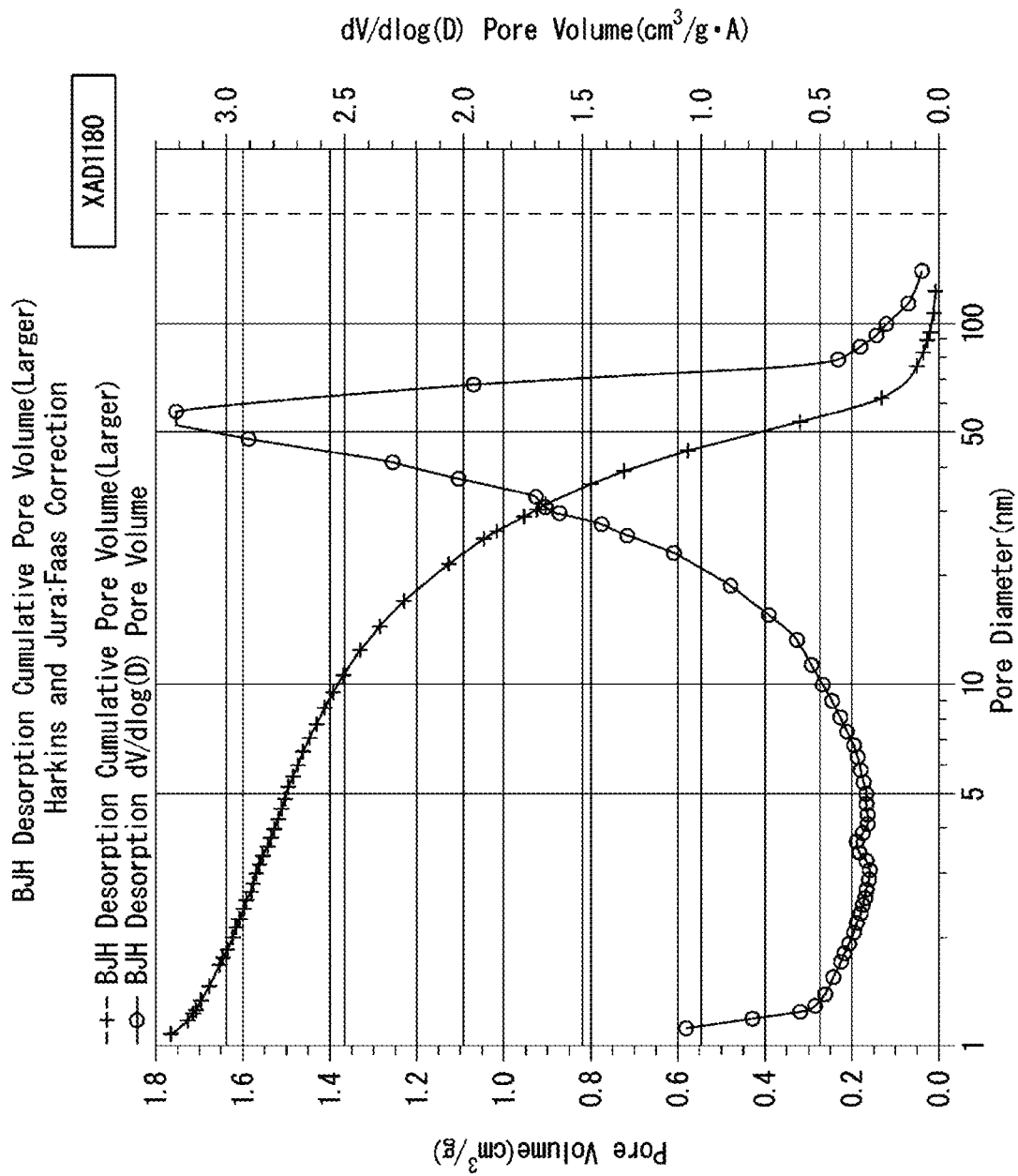
FIG. 1 is a graph of the Log differential pore volume distribution and cumulative pore volume of Amberlite™ XAD™ 1180N.

The blood purifier of the present embodiment has a body vessel and a porous formed article placed in the body vessel. The body vessel generally has a blood inlet, an internal space, and a blood outlet. The internal space can accommodate the porous formed article. For a blood purification process, in general, blood before processing is introduced to the internal space through the blood inlet and processed by contact with the porous formed article of the present embodiment present in the internal space. The blood thus processed can be discharged through the blood outlet. Examples of the shape of the body vessel can include, but are not limited to, tubular shapes, typically, cylindrical columns.

[Low-Melting Point Water Content]

The porous formed article comprises a hydrophobic polymer and a hydrophilic polymer, and has a low-melting point water content of 0.12 g or larger and 2.00 g or smaller, preferably 0.12 g or larger and 1.85 g or smaller, more preferably 0.37 g or larger and 1.85 g or smaller, per 1 g dry weight of the porous formed article. In one embodiment, the upper limit of the low-melting point water content may be 1.35 g or smaller.

It has been reported that the amount of intermediate water is increased in proportion to the amount of hydrophilic groups, for example, a methoxy group and a carbonyl group, on the surface of a polymer constituting a porous formed article. A larger amount of intermediate water is known to minimize the adsorption and denaturation of plasma proteins and to reduce the adhesiveness of platelets to the porous formed article and reduce platelet activation (e.g., NPL 1). Water adsorbed to the surface of a polymer constituting a porous formed article is classified into "non-freezing water" which interacts strongly with the hydrophilic groups of the polymer, "free water" which has no interaction with the hydrophilic groups, and "intermediate water" which interacts weakly with the hydrophilic groups. The intermediate water totally differs in influence on biointerface from normal water, which freezes at 0° C. The presence of the intermediate water is considered important for materials excellent in blood compatibility. In general, the "intermediate water" is defined as water that freezes at lower than 0° C. (e.g., NPL 2). By contrast, the present inventors have analyzed water contained in a porous formed article using the latest DSC and analysis systems as of the priority date and consequently revealed that water that interacts with hydrophilic groups in a polymer constituting the porous formed article and has important influence on blood compatibility is water that freezes at lower than 0.18° C. In the specification of the present application, the water that freezes at lower than 0.18° C. is defined as "low-melting point water". The "low-melting point water content" means the amount of water that freezes at lower than 0.18° C. and is adsorbed to the porous formed article.

Heretofore, the percentage of the "intermediate water" in water present on polymer surface has been considered to influence biointerface. Therefore, only the percentage of the "intermediate water" with respect to normal water which freezes at 0° C. has been focused on in the analysis of water on the surface of a polymer constituting a porous formed article. The present inventors have found for the first time that the amount of "low-melting point water", water that freezes at lower than 0.18° C., is not only important for blood compatibility with less hemolysis and a smaller amount of platelets attached, but also influences the adsorption rate of the porous formed article for phosphorus ions, cytokines and alarmins, etc.

Although not bound by any theory, the inventors predict the following reason why blood compatibility such as less hemolysis and a smaller amount of platelets attached is exhibited when the low-melting point water content per 1 g dry weight of the porous formed article is 0.12 g or larger and 2.00 g or smaller: this is because the adsorption of plasma proteins and the denaturation of plasma proteins are minimized as mentioned above. Cytokines and alarmins are low-molecular proteins and are therefore also considered easier to adsorb to the porous formed article in proportion to the "low-melting point water content". The adsorption of TNF-α and HMGB1 having a relatively large molecular weight also requires a high "low-melting point water content" to some extent, but tends to be slightly decreased in proportion to the "low-melting point water content" because of the influence of the molecular weight. A low-melting point water content of less than 0.12 g deteriorates the blood compatibility of the porous formed article, and elevates a pressure loss of the blood purifier due to the occurrence of hemolysis, an increased amount of platelets attached, etc. A low-melting point water content exceeding 2.00 g tends to reduce an adsorption rate for a cytokine TNF-α and an adsorption rate for an alarmin HMGB1.

In the production of the blood purifier of the present embodiment, it is necessary for obtaining a blood purifier having excellent blood compatibility and favorable cytokine adsorption performance to adjust the low-melting point water content per 1 g dry weight of the porous formed article to the range of 0.12 g or larger and 2.00 g or smaller. If the low-melting point water content per 1 g dry weight of the porous formed article is less than 0.12 g, blood compatibility is not excellent. Therefore, a pressure loss of the blood purifier after blood processing tends to be largely elevated. Furthermore, the cytokine adsorption performance of interest tends to be difficult to obtain. If the low-melting point water content per 1 g dry weight of the porous formed article exceeds 2.00 g, an adsorption rate for TNF-α, a cytokine having a relatively high molecular weight, tends to be reduced. Also, an adsorption rate for an alarmin high-mobility group box 1 (HMGB1) tends to be reduced.

[Cytokine Adsorption Rate]

The adsorption rate for cytokines except for TNF-α is 50% or more, preferably 60% or more, more preferably 70% or more. Such an adsorption rate is achievable by setting the low-melting point water content per 1 g dry weight of the porous formed article to 0.12 g or larger. The TNF-α adsorption rate is 30% or more, preferably 60% or more. Such an adsorption rate is achievable by setting the low-melting point water content per 1 g dry weight of the porous formed article to 0.12 g or larger and 2.00 g or smaller. A low-melting point water content exceeding 2.00 g per 1 g dry weight of the porous formed article is not preferred because the TNF-α adsorption rate tends to be less than 30%.

The adsorption rate for an alarmin high-mobility group box 1 (HMGB1) is 60% or more, preferably 65% or more, more preferably 90% or more. Such an adsorption rate is achievable by setting the low-melting point water content per 1 g dry weight of the porous formed article to 0.12 g or larger and 2.00 g or smaller. A low-melting point water content exceeding 2.00 g per 1 g dry weight of the porous formed article is not preferred because the HMGB1 adsorption rate tends to be less than 60%.

Preferably, an adsorption rate of 90% or more for the alarmin high-mobility group box 1 (HMGB1) is attained by allowing the porous formed article to contain a specific cytokine adsorbent mentioned later.

[Contact-Induced Change Rate]

The contact-induced change rate of the porous formed article for use in the blood purifier of the present embodiment is preferably 0% or more and 0.2% or less, more preferably 0% or more and 0.1% or less, still more preferably 0%. The contact-induced change rate is a change rate of a mass that is decreased by fine particles formed through partial break upon contact between porous formed articles by stirring, and serves as an index indicating the strength or fragility of the porous formed article. There has existed so far no index accurately indicating the strength or fragility of the porous formed article. However, the inventors of the present application have found that if the contact-induced change rate is higher than 0.2%, the porous formed article is broken by the contact between porous formed articles in transporting a blood purifier and in using a blood purifier in hemofiltration, and may become responsible for elevation in pressure loss of the blood purifier. The contact-induced change rate that falls within the range of 0% or more and 0.2% or less can prevent the formation of fine particles and provide a blood purifier having much better safety.

In the case of obtaining the porous formed article by coating the porous formed article with a hydrophilic polymer, it is preferred for adjusting the contact-induced change rate to within the range of 0% or more and 0.2% or less that the porous formed article before coating with a hydrophilic polymer should be made of a hydrophobic polymer. For the porous formed article comprising a cytokine adsorbent, a slurry solution for forming of the porous formed article preferably contains a water-insoluble hydrophilic polymer (having a high-molecular-weight cross-linked structure, which resists dissolution in water). The slurry solution for forming may contain polyvinylpyrrolidone. The polyvinylpyrrolidone is soluble in water, but has high affinity for the hydrophobic polymer. Therefore, the obtained porous formed article tends to be rich in residual polyvinylpyrrolidone. Examples of the polyvinylpyrrolidone include polyvinylpyrrolidone K90 (manufactured by BASF SE, weight-average molecular weight: 1,200,000). More preferably, the porous formed article is coated with the hydrophilic polymer.

[Body Vessel]

In one embodiment, ratio L/D of effective length L to cross-sectional diameter D of the blood purifier of the present embodiment is preferably 1.00 or more and 2.30 or less. The blood purifier having L/D of 1.00 or more is easy to produce. The blood purifier having L/D of 2.30 or less can be prevented from elevating a pressure loss after blood processing.

In the specification of the present application, the "effective length L" means a length in the longitudinal direction (generally, the blood flow direction) of a region occupied by the porous formed article in the internal space of the body vessel. The "equivalent circle diameter D" means an equivalent circle diameter at a cross section in the shorter direction (a direction perpendicular to the longitudinal direction) of the region occupied by the porous formed article in the internal space of the body vessel, and is calculated according to the following expression (1):

$$D = 2\sqrt{V/L/3.14} \quad (1)$$

In the expression (1), V represents an apparent volume of the region occupied by the porous formed article in the body vessel. The apparent volume V of the region occupied by the porous formed article means the volume of a region occupying the void space of the porous formed article, not the solid volume of the porous formed article.

The apparent volume V of the blood purifier of the present embodiment is preferably 210 mL or larger and 500 mL or smaller, more preferably 260 mL or larger and 500 mL or smaller, still more preferably 310 mL or larger and 500 mL or smaller, even more preferably 360 mL or larger and 500 mL or smaller. The apparent volume V of 210 mL or larger can exert rapid adsorption performance in flowing blood in a column. The apparent volume V of 500 mL or smaller is capable of reducing a priming volume in flowing blood in the blood purifier, and of reducing burdens on living bodies.

[Pressure Loss]

In one embodiment, the blood purifier of the present embodiment has a pressure loss of less than 13 kPa before blood processing and has a pressure loss of less than 13 kPa after blood processing, when an aqueous polyvinylpyrrolidone solution having a viscosity of 3.75 mPa·s or higher and 3.85 mPa·s or lower is flowed in the blood purifier at a passing rate of 400 mL/min. The pressure loss of less than 13 kPa before and after blood processing means that the blood purifier resists clogging even when filtering blood (processing blood) and facilitates blood filtration (blood processing).

The porous formed article having favorable cytokine adsorption performance easily adsorbs erythrocytes or platelets. In this respect, low blood compatibility of the porous formed article is responsible for clogging the blood purifier due to the adsorption and denaturation of plasma proteins and elevating a pressure loss. Hence, a blood purifier having a porous formed article, which has favorable cytokine adsorption performance and has a low pressure loss before and after blood processing has not been able to be prepared so far. By contrast, a porous formed article that suppresses the adsorption and denaturation of plasma proteins and is excellent in blood compatibility such as little hemolysis and a smaller amount of platelets attached to the porous formed article is obtained by setting the low-melting point water content to 0.12 g or larger. This attains adjustment of the pressure loss after blood processing to less than 13 kPa while favorable cytokine adsorption performance is maintained.

The aqueous polyvinylpyrrolidone solution can be prepared by adding polyvinylpyrrolidone (PVP, manufactured by BASF SE, K90) in small portions to 1 L of ultrapure water, stirring the mixture until completely dissolved, and measuring the viscosity of the obtained solution in a viscometer (TVE-25L, manufactured by Told Sangyo Co., Ltd.), and adding the polyvinylpyrrolidone thereto until the viscosity becomes 3.75 mPa·s or higher and 3.85 mPa·s or lower. In the specification of the present application, the pressure loss of the blood purifier means difference between the blood entry pressure and blood exit pressure of the blood purifier when the aqueous polyvinylpyrrolidone solution is flowed from the blood entry side (inlet) to the blood exit side (outlet) of the blood purifier at a passing rate of 400 mL/min.

The pressure loss can be compared between before and after blood processing. In this context, the "blood processing" means that blood is passed through the blood purifier by the following procedures: first, two 50 cm polyvinyl chloride tubes (manufactured by Naniwa Industry Co., Ltd.) each packed with saline (Otsuka Normal Saline, manufactured by Otsuka Pharmaceutical Factory) and clamped at one end with forceps are connected beforehand to the blood entry side (inlet) and blood exit side (outlet) of the blood purifier, respectively, so as not to mingle air thereinto. Next, their forceps are removed, and then, 2 L of saline is passed through the blood purifier from the blood entry side to the blood exit side at a passing rate of 100 mL/min using a blood pump to perform the saline priming of the blood purifier. In this respect, attention must be paid so as not to mingle air into the blood purifier. Subsequently, heparin sodium (Heparin Sodium Injection 50000 Units/50 mL, manufactured by Nipro Corp.) is added at a concentration of 2000 IU/L to human blood collected from a healthy volunteer to prepare 500 mL of heparin-supplemented human blood. The tube connected to the blood entry side of the blood purifier is replaced with one 50 cm polyvinyl chloride tube (manufactured by Naniwa Industry Co., Ltd.) packed with the human blood and clamped at one end with forceps, with attention paid so as not to mingle air thereinto. After removal of the forceps of the newly connected tube, 150 mL of the human blood is passed through the blood purifier from the blood entry side to the blood exit side at a passing rate of 100 mL/min to replace the contents in the blood purifier and the tubes with the human blood. Finally, 250 mL of the remaining human blood is added to a stainless beaker, and the inside of the beaker is gently stirred with a rotor. The tube connected to the blood entry side of the blood purifier and the tube connected to the blood exit side are placed in the blood in the beaker. Blood is circulated for 2 hours at a rate of 100 mL/min using a blood pump with attention paid so as not to mingle air into the blood purifier.

The pressure loss after blood processing is measured by the following procedures.

Blood remaining in the blood purifier is removed within 2 minutes after blood processing.

Within 2 minutes after removal of the blood, saline of 37° C. is passed through the blood purifier from the blood entry side (inlet) to the blood exit side (outlet) of the blood purifier by one pass for 15 minutes at a passing rate of 100 mL/min.

Within 2 minutes after removal of the remaining saline, the pressure loss of the blood purifier is measured by the method described above.

The measurement described above is performed in three blood purifiers, and an average value is regarded as the pressure loss after blood processing.

The blood purifier of the present embodiment is preferably a blood purifier for processing whole blood. The blood purifier of the present embodiment is suitable for removing cytokines and an alarmin high-mobility group box 1 (HMGB1) from human whole blood by contact with the human whole blood.

[Amount of Platelets Attached]

In one embodiment, the amount of platelets attached per 1 mL of blood when the blood is contacted with the porous formed article is preferably 400,000,000 platelets/mL or smaller, more preferably 350,000,000 platelets/mL or smaller, still more preferably 300,000,000 platelets/mL or smaller. The amount of platelets attached serves as an index for the blood compatibility of the porous formed article. When the amount of platelets attached to the porous formed article is 400,000,000 platelets/mL or smaller, elevation in the pressure loss of the blood purifier after blood processing can be suppressed. A porous formed article that suppresses the adsorption and denaturation of plasma proteins and is excellent in blood compatibility such as little hemolysis and a smaller amount of platelets attached to the porous formed article is obtained by setting the low-melting point water content to 0.12 g or larger. This attains adjustment of the amount of platelets attached to 400,000,000 platelets/mL or smaller.

[Cumulative Pore Volume]

The cumulative pore volume at pore diameters of 5 nm or larger and 100 nm or smaller of the porous formed article is preferably 0.5 cm$^3$/g or more, more preferably 0.8 cm$^3$/g or more, still more preferably 1.0 cm$^3$/g or more. The upper limit value of the cumulative pore volume is preferably 3.5 cm$^3$/g or less, more preferably 3.0 cm$^3$/g or less, still more preferably 2.5 cm$^3$/g or less. The cumulative pore volume that falls within the range described above is preferred because the porous formed article can remove more hydrophobic protein molecules because of more improved adsorbability of the polymer-supported porous formed article. When the cumulative pore volume falls within the range described above, an eluted biocompatible polymer can be more effectively adsorbed into the pores. As a result, a porous formed article that reduces the elution of the biocompatible polymer into blood while having more favorable blood compatibility can be obtained, which is preferred.

The cumulative pore volume at pore diameters of 100 nm or larger and 200 nm or smaller of the porous formed article is preferably 0.2 cm$^3$/g or less, more preferably 0.1 cm$^3$/g or less, still more preferably 0.05 cm$^3$/g or less. When the cumulative pore volume falls within the range described above, the porous formed article has many pores with a size suitable for the adsorption of hydrophobic protein molecules. As a result, a porous formed article having much better adsorbability can be obtained, which is preferred.

[Amount of Albumin Adsorbed]

The amount of albumin adsorbed to the porous formed article is preferably 13 mg/mL or larger and 90 mg/mL or smaller, more preferably 30 mg/mL or larger and 90 mg/mL or smaller, still more preferably 45 mg/mL or larger and 64 mg/mL or smaller. When the amount of albumin adsorbed is 13 mg/mL or larger, the cytokine adsorption performance of the porous formed article is improved. When the amount of albumin adsorbed is 90 mg/mL or smaller, reduction in the amount of albumin useful for human bodies can be suppressed.

[Shape, Etc. Of Porous Formed Article]

The porous formed article of the present embodiment can be in an arbitrary form such as a particle, threadlike, sheet, hollow fiber, circular cylinder, or hollow cylinder form and is preferably in the form of globular particles. The globular particles mean that the particles have a substantially globular shape, and may have a spherical or oval spherical shape. The area-average particle size of the globular particles is preferably 300 μm or larger and 1,000 μm or smaller, more preferably 400 μm or larger and 800 μm or smaller, still more preferably 500 μm or larger and 700 μm or smaller. The area-average particle size of 300 μm or larger can effectively suppress elevation in pressure in flowing blood in a column. The area-average particle size of 1,000 μm or smaller can exert rapid adsorption performance.

[Hydrophobic Polymer]

The hydrophobic polymer contained in the porous formed article can be any hydrophobic polymer that can form the porous formed article. Examples of the hydrophobic polymer include many types of polymers such as polysulfone polymers, polyethersulfone (PES) polymers, polyetherimide polymers, polyvinylidene fluoride polymers, polyvinylidene chloride polymers, polymethyl methacrylate (PMMA) polymers, polyimide polymers, polyarylethersulfone, polypropylene polymers, polystyrene polymers such as styrene-divinylbenzene copolymers, and polycarbonate polymers. Among them, aromatic polysulfone, aromatic polyethersulfone, and polystyrene polymers such as styrene-divinylbenzene copolymers are preferred because of their excellent heat stability, acid resistance, alkali resistance and mechanical strength. The hydrophobic polymer is not particularly limited by its degree of polymerization or molecular weight.

Examples of the aromatic polysulfone include polymers having a repeat unit represented by the following formula (2):

$$—O—Ar—C(CH_3)_2—Ar—O—Ar—SO_2—Ar— \quad (2)$$

wherein Ar represents a phenyl group 2-substituted at the para position.

The aromatic polysulfone is not particularly limited by its degree of polymerization or molecular weight.

Examples of the aromatic polyethersulfone include polymers having a repeat unit represented by the following formula (3):

$$—O—Ar—SO_2—Ar— \quad (3)$$

wherein Ar represents a phenyl group 2-substituted at the para position.

The aromatic polyethersulfone is not particularly limited by its degree of polymerization or molecular weight.

[Hydrophilic Polymer]

The hydrophilic polymer contained in the porous formed article is not particularly limited as long as the hydrophilic polymer is a biocompatible polymer that is swollen in water but is not dissolved in water. In the specification of the present application, the hydrophilic polymer is also referred to as a "biocompatible polymer". Examples of the hydrophilic polymer include polymers having one or more of a sulfonic acid group, a carboxyl group, a carbonyl group, an ester group, an amino group, an amide group, a cyano group, a hydroxyl group, a methoxy group, a phosphoric acid group, an oxyethylene group, an imino group, an imide group, an imino ether group, a pyridine group, a pyrrolidone group, an imidazole group, a quaternary ammonium group, and the like.

When the hydrophobic polymer is aromatic polysulfone, the hydrophilic polymer is preferably a polyvinylpyrrolidone (PVP) polymer.

Examples of the polyvinylpyrrolidone polymer include vinylpyrrolidone-vinyl acetate copolymers, vinylpyrrolidone-vinylcaprolactam copolymers, and vinylpyrrolidone-vinyl alcohol copolymers. The hydrophilic polymer preferably comprises at least one of these polymers. Among them, polyvinylpyrrolidone, a vinylpyrrolidone-vinyl acetate copolymer, or a vinylpyrrolidone-vinylcaprolactam copolymer is suitably used from the viewpoint of compatibility with a polysulfone polymer or a polyethersulfone polymer.

The hydrophilic polymer is preferably a polymer comprising a monomer represented by the following chemical formula (1) as a monomeric unit:

[Formula 2]

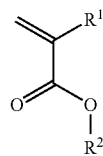
(1)

wherein $R^1$ represents a hydrogen atom or a methyl group, $R^2$ represents $—CH_2(CH_2)_qOC_tH_{2t+1}$ or $—CH_2C_mH_{2m+1}$, q represents 1 to 5, t represents 0 to 2, and m represents 0 to 17.

The monomer represented by the chemical formula (1) is more preferably at least one selected from the group consisting of 2-hydroxyethyl methacrylate (HEMA), 2-methoxyethyl methacrylate (MEMA), n-butyl methacrylate (BMA), and lauryl methacrylate (LMA), still more preferably 2-methoxyethyl methacrylate (MEMA). These monomers are preferred because the monomers can improve blood compatibility while maintaining higher excessive adsorbability of the porous formed article.

In one embodiment, it is preferred for the porous formed article that the hydrophilic polymer (biocompatible polymer) should be supported on the porous formed article of the hydrophobic polymer. It is more preferred that the biocompatible polymer represented by the chemical formula (1) should be supported thereon.

The content of the monomer represented by the chemical formula (1) is preferably 40% by mol or more, more preferably 60% by mol or more, with respect to all monomers constituting the biocompatible polymer. The upper limit value of the content of the monomer is not limited and may be 100% by mol or may be 80% by mol or less or 60% by mol or less, with respect to all monomers constituting the biocompatible polymer.

The biocompatible polymer preferably further comprises a charged monomer copolymerizable with the monomer represented by the chemical formula (1) as a monomeric unit. In the specification of the present application, the "charged monomer" is a monomer having a functional group that is partially or completely positively or negatively charged under a condition of pH 7.0. When the biocompatible polymer further comprises the charged monomer as a monomeric unit, its combination with the porous formed article can reduce the amount of the biocompatible polymer supported on the porous formed article and suppress reduction in adsorbability. Since the charged monomer has high hydrophilicity, biocompatibility is also improved. As a result, a porous formed article having more favorable adsorbability and blood compatibility tends to be obtained.

Examples of the charged monomer include monomers having at least one group selected from the group consisting of an amino group ($—NH_2$, $—NHR^3$, and $NR^3R^4$), a carboxyl group ($—COOH$), a phosphoric acid group ($—OPO_3H_2$), a sulfonic acid group ($—SO_3H$), and a zwitterionic group. In the amino group, $R^3$ and $R^4$ are each independently preferably an alkyl group having 1 to 3 carbon atoms, more preferably an alkyl group having 1 or 2 carbon atoms.

Among them, the charged monomer is more preferably a monomer having at least one group selected from the group consisting of an amino group, a carboxyl group, and a zwitterionic group. The charged monomer is still more preferably at least one selected from the group consisting of a cationic monomer having an amino group, an anionic monomer having a carboxyl group, a zwitterionic monomer having an amino group and a carboxyl group, and a zwitterionic monomer having an amino group and a phosphoric acid group. The charged monomer having a carboxyl group is still more preferred because the porous formed article can adsorb $Ca^{2+}$ and suppress increase in blood coagulation.

More specifically, the charged monomer is more preferably at least one selected from the group consisting of 2-aminoethyl methacrylate (AEMA), dimethylaminoethyl methacrylate (DMAEMA), diethylaminoethyl methacrylate (DEAEMA), [2-(methacryloyloxy)ethyl]trimethylammonium, acrylic acid (AAc), methacrylic acid (MAc), 2-(methacryloyloxy)ethyl phosphate, N-methacryloyloxyethyl-N,N-dimethylammonium-α-N-methylcarboxybetaine (CMB), [2-(methacryloyloxy)ethyl]dimethyl-(3-sulfopropyl)ammonium hydroxide (SPB), [3-(methacryloylamino)propyl]dimethyl(3-sulfopropyl)ammonium hydroxide (SPBA), 2-(methacryloyloxy)ethyl 2-(trimethylammonio)ethyl phosphate (MPC), and [3-(methacryloylamino)propyl]dimethyl (3-sulfobutyl)ammonium.

Among them, the charged monomer is more preferably at least one selected from the group consisting of methylaminoethyl methacrylate (DMAEMA), diethylaminoethyl methacrylate (DEAEMA), acrylic acid (AAc), N-methacryloyloxyethyl-N,N-dimethylammonium-α-N-methylcarboxybetaine (CMB), and 2-(methacryloyloxy)ethyl 2-(trimethylammonio)ethyl phosphate (MPC), still more preferably N-methacryloyloxyethyl-N,N-dimethylammonium-α-N-methylcarboxybetaine (CMB).

The content of the charged monomer is preferably 10% by mol or more and 60% by mol or less, more preferably 15% by mol or more and 40% by mol or less, with respect to all monomers constituting the biocompatible polymer. When the content of the charged monomer falls within the range described above, a porous formed article having excellent balance between impregnating properties into the porous formed article and hydrophilicity, and much better adsorbability and biocompatibility tends to be obtained.

The weight-average molecular weight (Mw) of the biocompatible polymer is preferably 5,000 or higher and 5,000,000 or lower, more preferably 10,000 or higher and 1,000,000 or lower, still more preferably 10,000 or higher and 300,000 or lower. The weight-average molecular weight of the biocompatible polymer that falls within the range described above is preferred from the viewpoint of moderate impregnating properties into the porous formed article, prevention of elution into blood, and reduction in the amount of the biocompatible polymer supported, etc. A method for analyzing the weight-average molecular weight (Mw) of the biocompatible polymer can be performed by measurement by, for example, gel permeation chromatography (GPC).

The biocompatibility (blood compatibility) of PMEA is described in detail in Masaru Tanaka, Materials biocompatibilizing surface of artificial organs, BIO INDUSTRY, Vol 20, No. 12, 59-70, 2003.

ATR-IR is known to be able to measure the infrared absorption of a penetration depth region because a wave incident on the sample is reflected by slightly penetrating the sample. The present inventors have found that the measurement region of this ATR-IR is almost equal to the depth of a "superficial layer" corresponding to the surface of the porous formed article. Specifically, the present inventors have found that: blood compatibility in the depth region almost equal to the measurement region of ATR-IR controls the blood compatibility of the porous formed article; and the presence of PMEA in this region can provide a blood purifier having given blood compatibility. The surface coating of the porous formed article with PMEA is also capable of preventing the formation of fine particles from the blood purifier after long-term storage.

The measurement region of ATR-IR depends on the wavelength of infrared light in air, the angle of incidence, the refractive index of prism, the refractive index of a sample, etc. and is a region within 1 μm from the surface.

The presence of PMEA on the surface of the porous formed article can be confirmed by the pyrolysis-gas chromatography-mass spectrometry of the porous formed article. The presence of PMEA is predicted if a peak is seen around 1735 $cm^{-1}$ in an infrared absorption curve in attenuated total reflection-infrared (ATR-IR) spectroscopy on the surface of the porous formed article. However, the peak therearound might be derived from other substances. Accordingly, 2-methoxyethanol derived from PMEA can be confirmed by pyrolysis-gas chromatography-mass spectrometry to confirm the presence of PMEA.

PMEA has unique solubility in a solvent. For example, PMEA is dissolved neither in a 100% ethanol solvent nor in a 100% methanol solvent, but is dissolved in a water/ethanol mixed solvent or a water/methanol mixed solvent in some regions depending on mixing ratios thereof. A larger amount of water at the mixing ratios within the regions where PMEA is dissolved enhances the peak intensity of a peak derived from PMEA (around 1735 $cm^{-1}$). The methanol:water ratio is preferably 80:20 to 40:60, more preferably 70:30 to 45:55, still more preferably 60:40 to 45:55, from the viewpoint of the solubility of PMEA and the amount of PMEA coating.

For the porous formed article comprising PMEA on the surface, product design is simple owing to little change in water penetration performance because change in surface pore size is small. In the present embodiment, the porous formed article has PMEA on the surface. For example, in the case of coating the porous formed article with PMEA, PMEA is considered to adhere thereto in an ultrathin membrane form and to coat the porous formed article surface substantially without blocking the pores. Particularly, PMEA, which has a small molecular weight and a short molecular chain, is preferred because the structure of the coating film is less likely to be thickened and the structure of the porous formed article is less likely to be changed. PMEA is preferred because PMEA has high compatibility with other substances and can be uniformly applied to the surface of the porous formed article, thereby improving blood compatibility.

The hemolysis of the porous formed article can be eliminated by uniformly applying PMEA to the surface of the porous formed article using a water/methanol mixed solvent containing PMEA.

For example, a method of injecting a coating solution of dissolved PMEA from above a column (vessel) packed with the porous formed article for coating is suitably used as a method for forming a PMEA-coated layer on the surface of the porous formed article.

The polyvinylpyrrolidone (PVP) polymer is not particularly limited, and polyvinylpyrrolidone (PVP) is suitably used.

[Porous Formed Article Comprising Cytokine Adsorbent]

The present inventors have found that in one embodiment, when the porous formed article comprises a specific cytokine adsorbent, a porous formed article having favorable cytokine adsorption performance and having favorable phosphorus adsorption performance is obtained using any hydrophobic polymer and/or hydrophilic polymer as a porous formed article material. This is a method totally different from the aforementioned method of supporting the biocompatible polymer on the hydrophobic polymer, and is a novel method for imparting favorable cytokine adsorption performance and favorable phosphorus adsorption performance to the blood purifier.

In healthy human adults having the normally functioning kidneys, excess phosphorus in the body is eliminated from the body, mainly as urine. On the other hand, renal disease patients, etc. having renal dysfunction, such as chronic renal failure patients cannot properly eliminate excess phosphorus from their bodies. Therefore, phosphorus is gradually accumulated in the body, causing a disease such as hyperphosphatemia. Sustained hyperphosphatemia causes secondary hyperparathyroidism resulting in renal osteodystrophy characterized by symptoms such as bone pain, fragility, deformation, and easy fracture. This, if combined with hypercalcemia, elevates the risk of developing cardiac failure ascribable to cardiovascular calcification. The cardiovascular calcification is one of the most serious complications of chronic renal failure or the like. Therefore, it is very important for preventing hyperphosphatemia in chronic renal failure patients to properly control the amount of phosphorus in the body.

For patients receiving hemodialysis, phosphorus accumulated in the body is regularly removed and adjusted by dialysis therapies such as hemodialysis, hemodiafiltration and hemofiltration so as not to lead to hyperphosphatemia. The dialysis therapies generally require a treatment time of 4 hours per run three times a week. However, if patients receiving hemodialysis ingest 1000 mg of phosphorus, which is ingested by healthy human adults in 1 day, phosphorus (650 mg) supposed to be eliminated from the kidneys is accumulated in an amount as large as 4550 mg in 1 week in the body. Usual hemodialysis is capable of removing approximately 800 to 1000 mg of phosphorus by one dialysis run and is capable of removing approximately 3000 mg of phosphorus by dialysis three times a week. The amount (3000 mg) of phosphorus that can be removed by the dialysis therapy falls short of the amount (4550 mg) of phosphorus accumulated in 1 week. As a result, phosphorus is accumulated in the body. Particularly, patients receiving maintenance dialysis, who are chronic renal failure patients, have lost their renal functions, the principal excretion pathway of phosphorus, and have therefore lost, almost completely, the function of eliminating phosphorus into urine. The fact is that the dialysis therapy can remove phosphorus from the body through the event of diffusion into a dialysate which contains no phosphorus, but cannot sufficiently eliminate phosphorus under the current dialysis time and dialysis conditions. Thus, the dialysis therapy alone is not sufficiently effective for removing phosphorus. Therefore, in order to control phosphorus, dietary therapy and drug therapy which involves drinking a phosphorus binder are practiced in addition to the dialysis therapy. The important thing is that patients' nutritional statuses are evaluated to confirm the absence of undernutrition, followed by the restriction of phosphorus intakes.

For the control of phosphorus, the CKD-MBD (chronic kidney disease-mineral and bone disorders) guideline reports that serum phosphorus levels are 3.5 to 6.0 mg/dL. A serum phosphorus level of 3.5 mg/dL or lower means hypophosphatemia which is responsible for rachitis or osteomalacia. A serum phosphorus level of 6.0 mg/dL or higher means hyperphosphatemia which is responsible for cardiovascular calcification. The dietary therapy which involves reducing phosphorus intakes has the difficulty in managing phosphorus concentrations in the body because of the balance between the dietary therapy and patients' nutritional statuses and also because patients' own preferences must be taken into consideration. The drug therapy manages phosphorus concentrations by medication before or during each meal with an oral drug of a phosphorus binder that forms insoluble phosphate through binding to a diet-derived phosphate ion in the digestive tract to suppress the absorption of phosphorus from the intestine. However, the drug therapy requires a considerably large amount of the phosphorus binder drunk at each meal. Hence, the medication with the phosphorus binder cause adverse reactions such as vomiting, a feeling of fullness, constipation, and drug accumulation in the body with high probability. Therefore, compliance with medication is very low (reportedly 50% or less) due to these adverse reactions. Thus, it is very difficult both for doctors and for patients to manage phosphorus concentrations using drugs.

The porous formed article comprising a cytokine adsorbent is capable of improving phosphorus adsorption performance and is also capable of largely improving an adsorption rate for an alarmin high-mobility group box 1 (HMGB1). In one embodiment, a porous formed article comprising a specific cytokine adsorbent and a specific hydrophilic polymer, preferably a polyvinylpyrrolidone (PVP) polymer, is capable of decreasing a cumulative pore volume at pore diameters of 5 nm or larger and 100 nm or smaller and is consequently capable of resisting adsorption of albumin, which is useful for human bodies. Furthermore, the porous formed article comprising a specific cytokine adsorbent and a specific hydrophilic polymer, preferably a polyvinylpyrrolidone (PVP) polymer, is capable of setting the adsorption rate for HMGB1 to 90% or more.

Exemplary solutions to the obtainment of a blood purifier excellent in blood compatibility and the obtainment of a blood purifier having a low pressure loss before and after blood processing among the problems to be solved by the present invention are disclosed in the section [Blood purifier]. Exemplary solutions to the obtainment of a safely usable blood purifier among the problems to be solved by the present invention will be disclosed in the section [Removal of fine particles].

[Cytokine Adsorbent]

In the specification of the present application, the cytokine adsorbent means an inorganic substance that exhibits the event of cytokine adsorption. The cytokine adsorbent can be contained in the porous formed article or can constitute the porous formed article.

Examples of the cytokine adsorbent composed of a natural product include various mineral substances such as zeolite and montmorillonite. Specific examples of the various mineral substances include kaolin mineral having a single layer lattice of aluminosilicate, white mica having a double layer lattice structure, glauconite, Kanuma soil, pyrophyllite, talc, feldspar having a three-dimensional skeleton structure, zeolite, and montmorillonite.

Examples of the cytokine adsorbent composed of a synthetic product include metal oxides, salts of polyvalent metals, and insoluble aqueous oxides. The metal oxides include composite metal oxides, composite metal hydroxides, aqueous oxides of metals, etc.

The cytokine adsorbent preferably contains at least one metal oxide represented by the following formula (4):

$$MN_xO_n \cdot mH_2O \qquad (4)$$

wherein x represents 0 to 3, n represents 1 to 4, m represents 0 to 6, and M and N each represent a metal element selected from the group consisting of Ti, Zr, Sn, Sc, Y, La, Ce, Pr, Nd, Sm, Eu, Gd, Tb, Dy, Ho, Er, Tm, Yb, Lu, Al, Si, Cr, Co, Ga, Fe, Mn, Ni, V, Ge, Nb, and Ta and are different from each other from the viewpoint of adsorption performance for objects to be adsorbed, particularly, cytokines. The metal oxide may be an anhydrous (unhydrated) metal oxide of the formula (4) wherein m is 0, or may be an aqueous oxide of a metal (hydrous metal oxide) of the formula (4) wherein m is a numerical value other than 0.

The metal oxide of the formula (4) wherein x is a numerical value other than 0 is a composite metal oxide in which each metal element contained is uniformly distributed throughout the oxide with regularity, and which is represented by a chemical formula having a fixed compositional ratio of each metal element contained in the metal oxide.

Specifically, the composite metal oxide forms a perovskite structure, a spinel structure, or the like, and includes nickel ferrite ($NiFe_2O_4$) and aqueous ferrite salt of zirconium ($Zr·Fe_2O_4·mH_2O$, wherein m represents 0.5 to 6). The cytokine adsorbent may contain a plurality of metal oxides represented by the formula (4).

The metal oxide as the cytokine adsorbent is preferably selected from the following groups (a) to (c):
(a) hydrous titanium oxide, hydrous zirconium oxide, hydrous tin oxide, hydrous cerium oxide, hydrous lanthanum oxide and hydrous yttrium oxide;
(b) a composite metal oxide of at least one metal element selected from the group consisting of titanium, zirconium, tin, cerium, lanthanum and yttrium with at least one metal element selected from the group consisting of aluminum, silicon and iron; and
(c) activated alumina from the viewpoint of being excellent in adsorption performance for objects to be adsorbed, particularly, cytokines.

A material selected from any of the groups (a) to (c) may be used, materials selected from any of the groups (a) to (c) may be used in combination, or respective materials of the groups (a) to (c) may be used in combination. For the combined use, a mixture of two or more materials selected from any of the groups (a) to (c) may be used, or a mixture of two or more materials selected from two or more of the groups (a) to (c) may be used.

The cytokine adsorbent may contain aluminum sulfate-impregnated activated alumina from the viewpoint of inexpensiveness and high adsorbability.

The cytokine adsorbent more preferably further contains a solid solution of a metal element other than M and N described above, in addition to the metal oxide represented by the formula (4), from the viewpoint of cytokine adsorbability and production cost. Examples thereof include a solid solution of iron in hydrous zirconium oxide represented by $ZrO_2·mH_2O$ (wherein m represents numerical value other than 0).

Examples of the salt of the polyvalent metal include hydrotalcite compounds represented by the following formula (5):

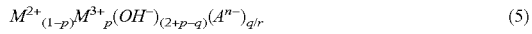

wherein $M^{2+}$ represents at least one divalent metal ion selected from the group consisting of $Mg^{2+}$, $Ni^{2+}$, $Zn^{2+}$, $Fe^{2+}$, $Ca^{2+}$, and $Cu^{2+}$, $M^{3+}$ represents at least one trivalent metal ion selected from the group consisting of $Al^{3+}$ and $Fe^{3+}$, $A^{n-}$ represents a n-valent anion, $0.1 \leq p \leq 0.5$, $0.1 \leq q \leq 0.5$, and r represents 1 or 2.

The hydrotalcite compounds represented by the formula (5) are preferred because raw materials are inexpensive as the cytokine adsorbent and the adsorbability is high.

Examples of the insoluble aqueous oxide include insoluble heteropolyacid salts and insoluble hexacyanoferrate salts.

Although a metal carbonate as the cytokine adsorbent has excellent performance from the viewpoint of adsorption performance, use of a carbonate requires discussing purposes from the viewpoint of elution.

At least one metal carbonate represented by the following formula (6):

$$Q y R z(CO_3)s·tH_2O \qquad (6)$$

wherein y represents 1 to 2, z represents 0 to 1, s represents 1 to 3, t represents 0 to 8, and Q and R each represent a metal element selected from the group consisting of Mg, Ca, Sr, Ba, Sc, Mn, Fe, Co, Ni, Ag, Zn, Y, La, Ce, Pr, Nd, Sm, Eu, Gd, Tb, Dy, Ho, Er, Tm, Yb, and Lu and are different from each other can be contained as the metal carbonate from the viewpoint that ion exchange reaction with a carbonate ion can be expected.

The metal carbonate may be an anhydrous (unhydrated) metal carbonate of the formula (6) wherein t is 0, or may be a hydrate of the formula (6) wherein t is a numerical value other than 0.

The cytokine adsorbent is preferably selected from the following group (d):
(d) magnesium carbonate, calcium carbonate, strontium carbonate, barium carbonate, scandium carbonate, manganese carbonate, iron carbonate, cobalt carbonate, nickel carbonate, silver carbonate, zinc carbonate, yttrium carbonate, lanthanum carbonate, cerium carbonate, praseodymium carbonate, neodymium carbonate, samarium carbonate, europium carbonate, gadolinium carbonate, terbium carbonate, dysprosium carbonate, holmium carbonate, erbium carbonate, thulium carbonate, ytterbium carbonate, and lutetium carbonate from the viewpoint of less elution and excellent adsorption performance for phosphorus, boron, fluorine and/or arsenic.

Elution of the metal carbonate and recrystallization of a metal ion on the metal carbonate with a cytokine are expected as cytokine adsorption mechanisms of the metal carbonate. Therefore, a higher solubility of the metal carbonate can be expected to offer a higher amount of cytokines adsorbed and better adsorption performance. Since metal elution from the cytokine adsorbent is of concern, use of the metal carbonate for purposes in which the metal elution becomes problematic needs to be sufficiently discussed.

The cytokine adsorbent constituting the porous formed article according to the present embodiment may contain impurity elements mingled due to its production method, etc. without inhibiting the function of the porous formed article. Examples of the impurity elements that may be mingled include nitrogen (nitric acid form, nitrous acid form, and ammonium form), sodium, magnesium, sulfur, chlorine, potassium, calcium, copper, zinc, bromine, barium and hafnium.

The cytokine adsorbent constituting the porous formed article according to the present embodiment may contain impurity elements mingled due to its production method, etc. without inhibiting the function of the porous formed article. Examples of the impurity elements that may be mingled include nitrogen (nitric acid form, nitrous acid form, and ammonium form), sodium, magnesium, sulfur, chlorine, potassium, calcium, copper, zinc, bromine, barium and hafnium.

A method for replacing water in the cytokine adsorbent with an organic liquid is not particularly limited. The cytokine adsorbent containing water may be dispersed in the organic liquid, then centrifuged, and filtered. Alternatively, the cytokine adsorbent may be filtered with a filter press or the like, and then, the organic liquid can be passed therethrough. In order to elevate a replacement rate, a method of dispersing the cytokine adsorbent in the organic liquid, followed by filtration is preferably repeated.

The replacement rate of moisture contained at the time of production with the organic liquid can be from 50% by mass to 100% by mass, preferably from 70% by mass to 100% by mass, more preferably from 80% by mass to 100% by mass. The replacement rate with the organic liquid refers to a value represented by the following expression (7):

$$Sb = 100 - Wc \qquad (7)$$

wherein Sb (% by mass) represents the replacement rate with the organic liquid, and Wc (% by mass) represents the moisture percentage of a filtrate after treatment of the cytokine adsorbent containing water with the organic liquid.

The moisture percentage (Wc) of a filtrate after treatment with the organic liquid can be measured by the Karl Fischer method.

Drying after the replacement of the moisture contained in the cytokine adsorbent with the organic liquid can suppress aggregation at the time of the drying, can increase the pore volume of the cytokine adsorbent, and can increase the adsorption capacity thereof. The replacement rate of 50% by mass or more with the organic liquid elevates the effect of suppressing aggregation at the time of drying and increases the pore volume of the cytokine adsorbent.

[Phosphorus Adsorption Performance of Porous Formed Article]

In one embodiment, the porous formed article of the present embodiment comprises a cytokine adsorbent and can be suitably used for phosphorus adsorption in the hemodialysis of patients receiving dialysis. Blood composition is divided into a plasma component and a blood cell component. The plasma component is constituted by 91% of water, 7% of proteins, a lipid component and inorganic salts. Phosphorus in blood is present as a phosphate ion in the plasma component. The blood cell component is constituted by 96% of erythrocytes, 3% of leukocytes and 1% of platelets. The erythrocytes have a size of 7 to 8 μm in diameter. The leukocytes have a size of 5 to 20 μm in diameter. The platelets have a size of 2 to 3 μm in diameter.

In one embodiment, the modal pore size of the porous formed article measured in a mercury porosimeter is 0.08 to 0.70 μm. In this case, phosphorus ions can be reliably adsorbed even by high-speed passing-through treatment because of a large abundance of an inorganic ion adsorbent on the outer surface, and adsorbability by the penetrant diffusion of the phosphorus ions to the inside of the porous formed article is also excellent. Furthermore, there is less reduction in blood flowability ascribable to the clogging, etc. of a blood cell component or the like. Such a porous formed article further having a biocompatible polymer on the surface can be more suitably used as a phosphorus binder for blood processing.

In one embodiment, the concentration of blood phosphorus returned into the body can be adjusted to almost 0 by employing a porous formed article having a modal pore size of 0.08 to 0.70 μm, and providing a biocompatible polymer on the surface of the porous formed article, thereby selectively and reliably adsorbing phosphorus ions in blood. The blood substantially free from phosphorus is returned into the body so that the transfer of phosphorus into blood from within or without cells is activated, presumably enhancing a refilling effect. Extracellular fluid or intracellularly existing phosphorus, which cannot usually be excreted, may probably be excreted by inducing the refilling effect of compensating for phosphorus in blood. This can properly manage phosphorus concentrations in blood in the body without causing adverse reactions in patients receiving dialysis, even if the patients receiving dialysis are not medicated with an oral drug of a phosphorus binder or are medicated with a small dose thereof (adjuvant use).

The blood purifier comprising a body vessel (column, etc.) packed with the porous formed article can be used such that such blood purifiers are connected, for example, in series or in parallel, upstream and downstream of a dialyzer at the time of dialysis. In one embodiment, the blood purifier of the present embodiment can be used as a blood purifier for phosphorus adsorption and is excellent in selectivity and adsorption performance for inorganic phosphorus even in a state with a low phosphorus concentration in blood and a fast space velocity. The blood purifier of the present embodiment is preferably used such that such blood purifiers are connected upstream and downstream of a dialyzer, from the viewpoint of easily inducing a refilling effect.

The phosphorus adsorption rate (%) (the percentage of adsorption of phosphorus in blood) is preferably 50% or more, more preferably 60% or more, still more preferably 70% or more, 80% or more, 85% or more, 90% or more, 95% or more, or 99% or more, from the viewpoint that a refilling effect can be expected.

[Removal of Fine Particles]

The blood purifier of the present embodiment is safely usable. The term "safely usable" preferably means that, for example, 3 months and 6 months after encapsulation of an injectable saline solution in the blood purifier, the number of 10 μm or larger fine particles in 1 mL of the injectable saline solution is 25 or less, and the number of 25 μm or larger fine particles therein is 3 or less; the absorbance of an eluate test solution is 0.1 or less; and the eluate test solution contains no membrane pore holding agent.

The present inventors have found that the fine particles to be formed from the blood purifier can be removed almost completely, preferably completely, by washing the porous formed article with a supercritical fluid or a subcritical fluid in the production of the blood purifier of the present embodiment.

The supercritical fluid means a fluid under conditions equal to or higher than critical pressure (hereinafter, also referred to as Pc) and equal to or higher than critical temperature (hereinafter, also referred to as Tc). The subcritical fluid means a fluid under conditions of $0.5<P/Pc<1.0$ and $0.5<T/Tc$, or $0.5<P/Pc$ and $0.5<T/Tc<1.0$ when reaction pressure and temperature are defined as P and T, respectively. The pressure and temperature ranges of the subcritical fluid are preferably $0.6<P/Pc<1.0$ and $0.6<T/Tc$, or $0.6<P/Pc$ and $0.6<T/Tc<1.0$. However, when the fluid is water, the temperature and pressure ranges of the subcritical fluid can be $0.5<P/Pc<1.0$ and $0.5<T/Tc$, or $0.5<P/Pc$ and $0.5<T/Tc<1.0$. In this context, the temperature is centigrade, and the expression representing the subcritical state is not limited thereto when either Tc or T is minus.

Water, an organic medium such as an alcohol, a gas such as carbon dioxide, nitrogen, oxygen, helium, argon, or air, or a mixed fluid thereof is used as the supercritical fluid or the subcritical fluid. Carbon dioxide is most preferred because the carbon dioxide can create a supercritical state even at a temperature on the order of ordinary temperature and well dissolves various substances.

[The Number of Fine Particles]

Blood purifiers for dialysis purposes need to satisfy the Approval Standards for Artificial Kidney Apparatus stipulated by Ministry of Health, Labour and Welfare, Japan, for obtaining the manufacturing (import) approval of dialysis type artificial kidney apparatuses. Thus, the blood purifier of the present embodiment needs to satisfy the standards for an eluate test described in the Approval Standards for Artificial Kidney Apparatus. For the blood purifier of the present embodiment, preferably, 3 months and 6 months after encapsulation of an injectable saline solution in the blood purifier, the number of 10 μm or larger fine particles in 1 mL of the saline solution is 25 or less, and the number of 25 μm or larger fine particles in 1 mL of the saline solution is 3 or less; and the absorbance of an eluate test solution is 0.1 or less.

A method for measuring the number of fine particles in an injectable saline solution encapsulated in the blood purifier is as follows.

(1) Measurement Method for Wet Type Blood Purifier

For the wet type blood purifier, a solution (e.g., UF filtration membrane water) is encapsulated in the blood purifier immediately before shipment, and radiation sterilization is performed in the solution, followed by the shipment of the blood purifier as it is. The solution in such a wet type blood purifier is completely removed, and 10 L of an injectable saline solution is passed through the porous formed article in the blood purifier (when the porous formed article is a hollow fiber membrane, filtered from the membrane inner surface side to the membrane outer surface side). Then, a fresh injectable saline solution is encapsulated in the blood purifier, which is then incubated at 25° C.±1° C. and stored while left standing for 3 months. The sampling of the saline solution from the blood purifier is performed after the whole solution (packed solution) is taken out of the blood purifier as much as possible and then uniformly mixed. For example, after sampling for measurement at 3 months after the start of storage, the remaining saline solution is brought back to the blood purifier, which is then hermetically sealed, stored for another 3 months, and used in measurement at 6 months after the start of storage.

(2) Measurement Method for Dry Type Blood Purifier

For the dry type blood purifier, radiation sterilization is not performed in a solution in many cases, and the blood purifier is often shipped in a dry state. 10 L of an injectable saline solution is passed through the porous formed article in the blood purifier (when the porous formed article is a hollow fiber membrane, filtered from the membrane inner surface side to the membrane outer surface side). Then, a fresh injectable saline solution is encapsulated in the blood purifier, which is then incubated at 25° C.±1° C. and stored while left standing for 3 months. The sampling of the saline solution from the blood purifier is performed after the whole solution (packed solution) is taken out of the blood purifier as much as possible and then uniformly mixed. For example, after sampling for measurement at 3 months after the start of storage, the remaining saline solution is brought back to the blood purifier, which is then hermetically sealed, stored for another 3 months, and used in measurement at 6 months after the start of storage.

The number of fine particles in the sampled solution (or the packed solution) is measurable with a particle counter.

The raw material for the vessel (column) of the blood purifier of the present embodiment is not limited, and, for example, a polystyrene polymer, a polysulfone polymer, a polyethylene polymer, a polypropylene polymer, a polyester polymer, a polyethylene tetrafluoride polymer, a polycarbonate polymer, a copolymer consisting of vinyl aromatic hydrocarbon and conjugated diene, or a mixed resin such as an acrylonitrile-butadiene-styrene block copolymer (ABS) can be used. A polyethylene polymer or a polypropylene polymer is preferably used from the viewpoint of cost of the raw material. Alternatively, a thermosetting resin, for example, polyurethane or epoxy, may be used for sealing.

[Method for Producing Porous Formed Article]

A method for producing the porous formed article of the present embodiment is not limited. Examples of the method for producing the porous formed article of the present embodiment include a method comprising supporting a hydrophilic polymer (biocompatible polymer) on the surface of a porous formed article constituted by a hydrophobic polymer. The details of the hydrophobic polymer and the biocompatible polymer according to the present embodiment, and their monomers are mentioned above, so that the description is omitted here.

In the present embodiment, a method for producing the biocompatible polymer is not limited. Examples of the method for producing the biocompatible polymer include a method comprising: preparing a monomer solution containing a monomer of the chemical formula (1) in an arbitrary solvent; adding an arbitrary polymerization initiator to the monomer solution to prepare a polymerization solution; and polymerizing the monomer.

In addition to the monomer of the chemical formula (1), a charged monomer may be further added into the monomer solution and/or into the polymerization solution, and thereby copolymerized with the monomer of the chemical formula (1). The details of the charged monomer are mentioned above, so that the description is omitted here.

In the present embodiment, the biocompatible polymer thus obtained by polymerization can be purified by an arbitrary purification method, for example, reprecipitation, dialysis, ultrafiltration, or extraction. The purified biocompatible polymer can be dried by an arbitrary drying method, for example, drying under reduced pressure, spray drying, freeze drying, and drying by heating.

An arbitrary supporting method, for example, application, spraying, or dipping, can be used as a method for supporting the biocompatible polymer on the surface of the porous formed article.

For example, the dipping method involves preparing a coating solution containing the biocompatible polymer dissolved in an arbitrary solvent, for example, an alcohol, chloroform, acetone, tetrahydrofuran, or dimethylformamide, and immersing the porous formed article in the coating solution. After impregnation, the porous formed article is taken out of the coating solution, and an extra solution is removed therefrom. Subsequently, the porous formed article can be dried by an arbitrary drying method. Examples of the drying method include air drying which is performed in a dry gas, and drying under reduced pressure which involves performing drying at ordinary temperature or under heating in a reduced-pressure atmosphere. Drying under reduced pressure is preferred from the viewpoint of decreasing the amount of the polymer per 1 g of the porous formed article according to the present embodiment.

The application method and the spraying method involve, for example, applying or spraying the coating solution to the porous formed article, followed by drying as described above.

[Method for Producing Porous Formed Article Comprising Cytokine Adsorbent]

Next, a method for producing the porous formed article of the present embodiment comprising a cytokine adsorbent will be described in detail.

The method for producing the porous formed article of the present embodiment comprising a cytokine adsorbent comprises, for example, the steps of:

(1) drying a cytokine adsorbent;
(2) milling the cytokine adsorbent obtained in the step (1);
(3) mixing the cytokine adsorbent obtained in the step (2) with a good solvent for hydrophobic polymers, a hydrophobic polymer, and optionally, a hydrophilic polymer to prepare slurry;
(4) shaping the slurry obtained in the step (3); and
(5) coagulating the shaped product obtained in the step (4) in a poor solvent.

Step (1): Step of Drying Cytokine Adsorbent

In the step (1), a cytokine adsorbent is dried to obtain a powder. In this respect, it is preferred for suppressing aggregation at the time of drying to perform the drying after replacement of moisture contained at the time of production with an organic liquid. The organic liquid is not particularly limited as long as the organic liquid is effective for suppressing the aggregation of the cytokine adsorbent. A highly hydrophilic liquid is preferably used. Examples thereof include alcohols, ketones, esters, and ethers.

The replacement rate with the organic liquid is preferably from 50% by mass to 100% by mass, more preferably from 70% by mass to 100% by mass, still more preferably from 80% by mass to 100% by mass.

A method for replacing the moisture with the organic liquid is not particularly limited. The cytokine adsorbent containing water may be dispersed in the organic liquid, then centrifuged, and filtered. Alternatively, the cytokine adsorbent may be filtered with a filter press or the like, and then, the organic liquid can be passed therethrough. In order to elevate a replacement rate, a method of dispersing the cytokine adsorbent in the organic liquid, followed by filtration is preferably repeated. The replacement rate with the organic liquid is determined by measuring the moisture percentage of a filtrate according to the Karl Fischer method.

Drying after the replacement of the moisture contained in the cytokine adsorbent with the organic liquid can suppress aggregation at the time of the drying, can increase the pore volume of the cytokine adsorbent, and can increase the adsorption capacity thereof. The replacement rate of 50% by mass or more with the organic liquid elevates the effect of suppressing aggregation at the time of drying and increases the pore volume of the cytokine adsorbent.

Step (2): Step of Milling Cytokine Adsorbent

In the step (2), the powder of the cytokine adsorbent obtained in the step (1) is milled. A milling method is not particularly limited, and dry milling or wet milling can be used.

The dry milling method is not particularly limited, and, for example, an impact mill such as a hammer mill, an air flow mill such as a jet mill, a medium mill such as a ball mill, or a compression mill such as a roller mill can be used. Among them, an air flow mill is preferred because the particle size distribution of the milled cytokine adsorbent can be sharp.

The wet milling method is not particularly limited as long as the wet milling method can mill and mix the cytokine adsorbent and the good solvent for hydrophobic polymers together. An approach for use in physical homogenization methods such as disruption under pressure, mechanical grinding, and sonication can be used.

Specific examples of the milling and mixing approach include generator shaft type homogenizers, blenders such as Waring blenders, medium stirring type mills such as sand mills, ball mills, attritors, and molding mills, jet mills, mortars and pestles, grinders, and sonicators. Among them, a medium stirring type mill is preferred because the medium stirring type mill has high milling efficiency and can mill even a highly viscous substance.

A ball size for use in the medium stirring type mill is not particularly limited and is preferably from 0.1 mm to 10 mm. The mill having a ball size of 0.1 mm or larger has milling force because of a sufficient ball mass and thus has high milling efficiency. The mill having a ball size of 10 mm or smaller is excellent in fine milling ability.

Examples of the material for the balls for use in the medium stirring type mill include, but are not particularly limited to, metals such as iron and stainless, oxides such as alumina and zirconia, and various non-oxide ceramics such as silicon nitride and silicon carbide. Among them, zirconia is excellent because of its excellent abrasion resistance and less contamination of products (mingling of abrasive substances).

The cytokine adsorbent thus milled is preferably filtered through a filter or the like and purified, in a state sufficiently dispersed in a good solvent for hydrophobic polymers.

The particle size of the milled and purified cytokine adsorbent is from 0.001 to 10 µm, preferably from 0.001 to 2 µm, more preferably from 0.01 to 0.1 µm. A smaller particle size is more preferred for uniformly dispersing the cytokine adsorbent in a dope. Homogeneous fine particles smaller than 0.001 µm tend to be difficult to produce. A cytokine adsorbent having a particle size exceeding 10 µm tends to render the porous formed article difficult to produce stably.

Step (3): Step of Preparing Slurry

In the step (3), the cytokine adsorbent obtained in the step (2) is mixed with a good solvent for hydrophobic polymers, a hydrophobic polymer, and optionally, a hydrophilic polymer to prepare slurry.

The good solvent for hydrophobic polymers for use in the step (2) and the step (3) is not particularly limited as long as the good solvent stably dissolves more than 1% by mass of the hydrophobic polymer under production conditions for the porous formed article. A conventional good solvent known in the art can be used.

Examples of the good solvent include N-methyl-2-pyrrolidone (NMP), N,N-dimethylacetamide (DMAC), and N,N-dimethylformamide (DMF). Only one of these good solvents may be used, or two or more thereof may be used as a mixture.

The amount of the hydrophobic polymer added in the step (3) is preferably from 3% by mass to 40% by mass, more preferably from 4% by mass to 30% by mass, in terms of the percentage of hydrophobic polymer/(hydrophobic polymer+hydrophilic polymer+good solvent for hydrophobic polymers). When the content percentage of the hydrophobic polymer is 3% by mass or more, a porous formed article having high strength is obtained. When the content percentage is 40% by mass or less, a porous formed article having a high porosity is obtained.

In the step (3), the hydrophilic polymer is not necessarily required to be added. The addition of the hydrophilic polymer homogenously produces a porous formed article having a fibrous structure forming a three-dimensionally continuous network structure on the outer surface and in the inside of the porous formed article, i.e., facilitates pore size control. Thus, a porous formed article that can reliably adsorb ions even by high-speed passing-through treatment is obtained.

The hydrophilic polymer for use in the step (3) is not particularly limited as long as the hydrophilic polymer is compatible with the good solvent for hydrophobic polymers and the hydrophobic polymer. Any of a natural polymer, a semisynthetic polymer, and a synthetic polymer can be used as the hydrophilic polymer.

Examples of the natural polymer include guar gum, locust bean gum, carrageenan, gum arabic, tragacanth, pectin, starch, dextrin, gelatin, casein, and collagen.

Examples of the semisynthetic polymer include methylcellulose, ethylcellulose, hydroxyethylcellulose, ethylhydroxyethylcellulose, carboxymethyl starch, and methyl starch.

Examples of the synthetic polymer include polyvinyl alcohol, polyvinylpyrrolidone (PVP), polyvinyl methyl ether, carboxyvinyl polymers, sodium polyacrylate, polyethylene glycols such as tetraethylene glycol and triethylene glycol.

Among them, a synthetic polymer is preferred from the viewpoint of enhancing supportability for the cytokine adsorbent. Polyvinylpyrrolidone (PVP) is more preferred from the viewpoint of improving porosity.

The weight-average molecular weight of the polyvinylpyrrolidone (PVP) is preferably from 1,100,000 to 35,000,000, more preferably from 1,200,000 to 35,000,000. A porous formed article excellent both in cytokine adsorption performance and in HMGB1 adsorption performance tends to be difficult to obtain unless polyvinylpyrrolidone (PVP) having a weight-average molecular weight of 1,100,000 or higher is used. The mass-average molecular weight of the hydrophilic polymer can be measured by gel permeation chromatography (GPC) analysis after dissolution of the hydrophilic polymer in a predetermined solvent.

The amount of the hydrophilic polymer added is preferably from 0.1% by mass to 40% by mass, more preferably from 0.1% by mass to 30% by mass, still more preferably from 0.1% by mass to 10% by mass, in terms of the percentage of the hydrophilic polymer/(hydrophilic polymer+hydrophobic polymer+good solvent for hydrophobic polymers).

When the amount of the hydrophilic polymer added is 0.1% by mass or more, a porous formed article having a fibrous structure forming a three-dimensionally continuous network structure on the outer surface and in the inside of the porous formed article is homogeneously obtained. When the amount of the hydrophilic polymer added is 40% by mass or less, an outer surface aperture ratio is appropriate. Thus, a porous formed article that can reliably adsorb ions even by high-speed passing-through treatment is obtained because of a large abundance of the cytokine adsorbent on the outer surface of the porous formed article.

Step (4): Shaping Step

In the step (4), the slurry obtained in the step (3) (slurry for shaping) is shaped. The slurry for shaping is mixed slurry of the hydrophobic polymer, the good solvent for hydrophobic polymers, the cytokine adsorbent, and optionally, the hydrophilic polymer.

The form of the porous formed article of the present embodiment can adopt an arbitrary form such as a particle, threadlike, sheet, hollow fiber, circular cylinder, or hollow cylinder form, depending on a method for shaping the slurry for shaping. Examples of the method for shaping the slurry into a particle form, for example, the form of globular particles, include, but are not particularly limited to, a rotary nozzle method which involves scattering the slurry for shaping contained in a rotary container from a nozzle disposed on the side of the container, to form liquid droplets. The rotary nozzle method can shape the slurry into the form of particles with a uniform particle size distribution. Specific examples of the rotary nozzle method include a method of spraying the slurry for shaping from a single-fluid nozzle or a two-fluid nozzle, followed by coagulation in a coagulation bath. The size of the nozzle is preferably from 0.1 mm to 10 mm, more preferably from 0.1 mm to 5 mm. The nozzle having a size of 0.1 mm or larger easily scatters liquid droplets. The nozzle having a size of 10 mm or smaller offers a uniform particle size distribution.

The centrifugal force is indicated by a centrifugal acceleration and is preferably from 5 G to 1500 G, more preferably from 10 G to 1000 G, still more preferably from 10 G to 800 G. The centrifugal acceleration of 5 G or more facilitates formation and scattering of liquid droplets. The centrifugation acceleration of 1500 G or less can prevent the slurry for shaping from being discharged without becoming a threadlike form and from widening a particle size distribution. Owing to a narrow particle size distribution, uniform water flow paths are formed when a column is packed with the porous formed article. This is advantageous for the absence of leakage (breakthrough) of cytokines (objects to be adsorbed) from the initial stage of water passing even by use of ultrahigh-speed passing-through treatment with water.

Examples of the method for shaping the slurry into a threadlike or sheet form include a method of extruding the slurry for shaping from a spinneret or a die having the corresponding shape, followed by coagulation in a poor solvent.

The method for forming the porous formed article in a hollow fiber form employs a spinneret consisting of an annular orifice, and this form of the porous formed article can thereby be formed in the same way as in the method for forming the porous formed article in a threadlike or sheet form.

In the method for forming the porous formed article in a circular cylinder or hollow cylinder form, the slurry for shaping, when extruded from a spinneret, may be coagulated in a poor solvent while cut, or may be cut after being coagulated into a threadlike form.

Step (5): Coagulation Step

In the step (5), the shaped product with its coagulation promoted, obtained in the step (4) is coagulated in a poor solvent to obtain a porous formed article.

In the step (5), a solvent in which the solubility of the hydrophobic polymer is 1% by mass or less under conditions of the step (5) can be used as the poor solvent. Examples thereof include water, alcohols such as methanol and ethanol, ethers, and aliphatic hydrocarbons such as n-hexane and n-heptane. Among them, water is preferred as the poor solvent.

In the step (5), the good solvent is brought from the preceding steps so that the concentration of the good solvent varies between the start and the end of the coagulation step. Hence, a poor solvent supplemented with the good solvent in advance may be used. The coagulation step is preferably performed by managing the concentration while separately adding water or the like so as to maintain the initial concentration.

The structure (outer surface aperture ratio and particle shape) of the porous formed article can be controlled by adjusting the concentration of the good solvent. When the poor solvent is water or a mixture of the good solvent for hydrophobic polymers and water, the content of the good solvent for hydrophobic polymers with respect to water in the coagulation step is preferably from 0 to 80% by mass, more preferably from 0 to 60% by mass.

The content of 80% by mass or less of the good solvent for hydrophobic polymers is effective for improving the shape of the porous formed article.

The temperature of the poor solvent is preferably from 40 to 100° C., more preferably from 50 to 100° C., still more preferably from 60 to 100° C., from the viewpoint of controlling the temperature and humidity of a spatial portion in a rotary container that scatters liquid droplets through centrifugal force as described below.

[Production Apparatus for Porous Formed Article in Particle Form]

When the porous formed article according to the present embodiment is in the form of particles, a production apparatus therefor can be a production apparatus comprising a rotary container which scatters liquid droplets through centrifugal force, and a coagulation vessel which retains a coagulating liquid, and further comprising a control unit which has a cover put over a spatial portion between the rotary container and the coagulation vessel, and controls the temperature and humidity of the spatial portion.

The rotary container which scatters liquid droplets through centrifugal force is not limited by a specific structure as long as the rotary container has the function of making the slurry for shaping into globular liquid droplets and scattering the liquid droplets through centrifugal force. Examples thereof include well-known rotary disks and rotary nozzles.

The rotary disk is configured in such a way that the slurry for shaping is supplied to the center of the rotating disk and then developed in a film form with a uniform thickness along the surface of the rotating disk so that the slurry is split dropwise through centrifugal force from the rim of the disk to scatter very small liquid droplets.

The rotary nozzle is configured in such a way that a large number of through-holes are formed in the peripheral wall of a hollow disc-shaped rotary container, or a nozzle is attached to the rotary container so as to penetrate the peripheral wall, and the slurry for shaping is supplied into the rotary container while the rotary container is rotated so that the slurry for shaping is discharged through centrifugal force from the through-holes or the nozzle to form liquid droplets.

The coagulation vessel which retains a coagulating liquid is not limited by a specific structure as long as the coagulation vessel has the function of being capable of retaining the coagulating liquid. Examples thereof include well-known coagulation vessels having an upper opening, and coagulation vessels having a structure where the coagulating liquid spontaneously flows downward through gravity along the inner face of a tubular body disposed so as to surround the rotary container. The coagulation vessel having an upper opening is an apparatus in which the liquid droplets scattered in the horizontal direction from the rotary container spontaneously flow downward and are captured by the surface of the coagulating liquid retained in the coagulation vessel having an upper opening. The coagulation vessel having a structure where the coagulating liquid spontaneously flows downward through gravity along the inner face of a tubular body disposed so as to surround the rotary container is an apparatus in which the coagulating liquid is discharged in almost equal flow volumes in the circumferential direction along the inner face of the tubular body and spontaneously flows downward along the inner face so that the liquid droplets are captured into the coagulating liquid flow and coagulated.

The control unit for the temperature and humidity of the spatial portion is a unit which has a cover put over a spatial portion between the rotary container and the coagulation vessel and controls the temperature and humidity of the spatial portion. The cover put over the spatial portion is not limited by a specific structure as long as the cover has the function of isolating the spatial portion from the external environment and facilitating practically controlling the temperature and humidity of the spatial portion. The cover can have, for example, a box, tubular, or umbrella shape. Examples of the material for the cover include metallic stainless steels and plastics. The cover may be covered with a heat insulation material known in the art from the viewpoint of isolation from the external environment. The cover may be provided with a partial opening for temperature and humidity adjustment.

The control unit for the temperature and humidity of the spatial portion is not limited by a specific unit as long as the control unit has the function of controlling the temperature and humidity of the spatial portion. Examples thereof include heaters such as electric heaters and steam heaters, and humidifiers such as ultrasonic humidifiers and heating humidifiers. A unit of warming the coagulating liquid retained in the coagulation vessel and controlling the temperature and humidity of the spatial portion through the use of steam generated from the coagulating liquid is preferred from the viewpoint of a convenient structure.

[Method for Forming Coating Layer of Hydrophilic Polymer]

Hereinafter, a method for forming a coating layer of the hydrophilic polymer (biocompatible polymer) on the surface of the porous formed article will be described.

In one embodiment, a coating solution containing the hydrophilic polymer can be applied to the surface of the porous formed article to form a coating film of the hydrophilic polymer. Hereinafter, the case of using, for example, PMEA, as the hydrophilic polymer will be mentioned. The PMEA coating solution may enter the pores formed in the porous formed article so that PMEA is contained throughout the pore surface of the porous formed article without largely changing the pore size of the porous formed article surface.

The solvent in the PMEA coating solution is not particularly limited as long as the solvent does not dissolve the polymers, such as the hydrophobic polymer and the hydrophilic polymer, constituting the porous formed article, and can dissolve or disperse PMEA. The solvent is preferably water or an aqueous alcohol solution because of process safety and good handling in a subsequent drying step. Water, an aqueous ethanol solution, an aqueous methanol solution, an aqueous isopropyl alcohol solution, a water/ethanol mixed solvent, a water/methanol mixed solvent, or the like is suitably used as the solvent from the viewpoint of a boiling point and toxicity. The type and composition of the solvent in the coating solution can be appropriately set in relation to the polymers constituting the porous formed article.

The concentration of PMEA in the PMEA coating solution is not limited and can be, for example, from 0.001% by mass to 1% by mass, more preferably from 0.005% by mass to 0.2% by mass, of the coating solution.

A method for applying the coating solution is not limited, and can adopt, for example, a method which involves packing an appropriate column (vessel) with the porous formed article, injecting the coating solution containing PMEA from above, and subsequently removing an extra solution using compressed air.

Then, the remaining unnecessary solvent is replaced and removed by washing with distilled water or the like. Then, the resultant can be sterilized and used as a medical tool.

If the porous formed article is dried after coating of the hydrophobic polymer with the hydrophilic polymer and before preparation of the blood purifier, the low-melting point water content of 0.12 g or larger is difficult to obtain. This is because the drying causes structural change in methoxy group and carbonyl group in the polymers constituting the porous formed article so that the polymers constituting the porous formed article tend to have the difficulty in retaining low-melting point water. Thus, it is preferred to involve no drying step between after coating of the hydrophobic polymer with the hydrophilic polymer and before preparation of the blood purifier. This can improve the low-melting point water content and consequently facilitates reducing the amount of platelets attached.

EXAMPLES

Hereinafter, the present embodiment will be specifically described with reference to Examples and Comparative <<Evaluation and Measurement Methods>>
[Area-Average Particle Size of Porous Formed Article]

The area-average particle size of porous beads was determined by measuring porous beads swollen with ultrapure water using a particle size distribution measurement apparatus (MT3300II, manufactured by MicrotracBEL Corp.) and calculating their area average as the area-average particle size (μm).

[Cumulative Pore Volume of Porous Formed Article]

The porous formed article swollen with ultrapure water was frozen and then freeze-dried for 24 hours to dry the porous formed article. The porous formed article thus dried was degassed (dried under reduced pressure) at 60° C. for 15 hours using VacPrep 061 (manufactured by Shimadzu Corp.-Micromeritics Instrument Corp.). Then, the cumulative pore volume ($cm^3/g$) was measured by the $N_2$ gas adsorption method using TriStar II 3020 (manufactured by Shimadzu Corp.-Micromeritics Instrument Corp.). In this respect, a desorption cumulative pore volume based on the BJH method was adopted as the cumulative pore volume. The measurement described above was performed ten times, and an average value of 8 values excluding the largest and smallest values was used.

[Specific Surface Area of Porous Formed Article]

The porous formed article thus dried as described above was degassed (dried under reduced pressure) at 60° C. for 15 hours using VacPrep 061 (manufactured by Shimadzu Corp.-Micromeritics Instrument Corp.). Then, the specific surface area ($m^2/g$) was measured by the $N_2$ gas adsorption method using TriStar II 3020 (manufactured by Shimadzu Corp.-Micromeritics Instrument Corp.). In this respect, a value based on a BET plot was adopted as the specific surface area. The measurement described above was performed ten times, and an average value of 8 values excluding the largest and smallest values was used.

[Low-Melting Point Water Content]

The "low-melting point water content per 1 g dry weight" of the porous formed article was measured by the following procedures.

Figure 2:
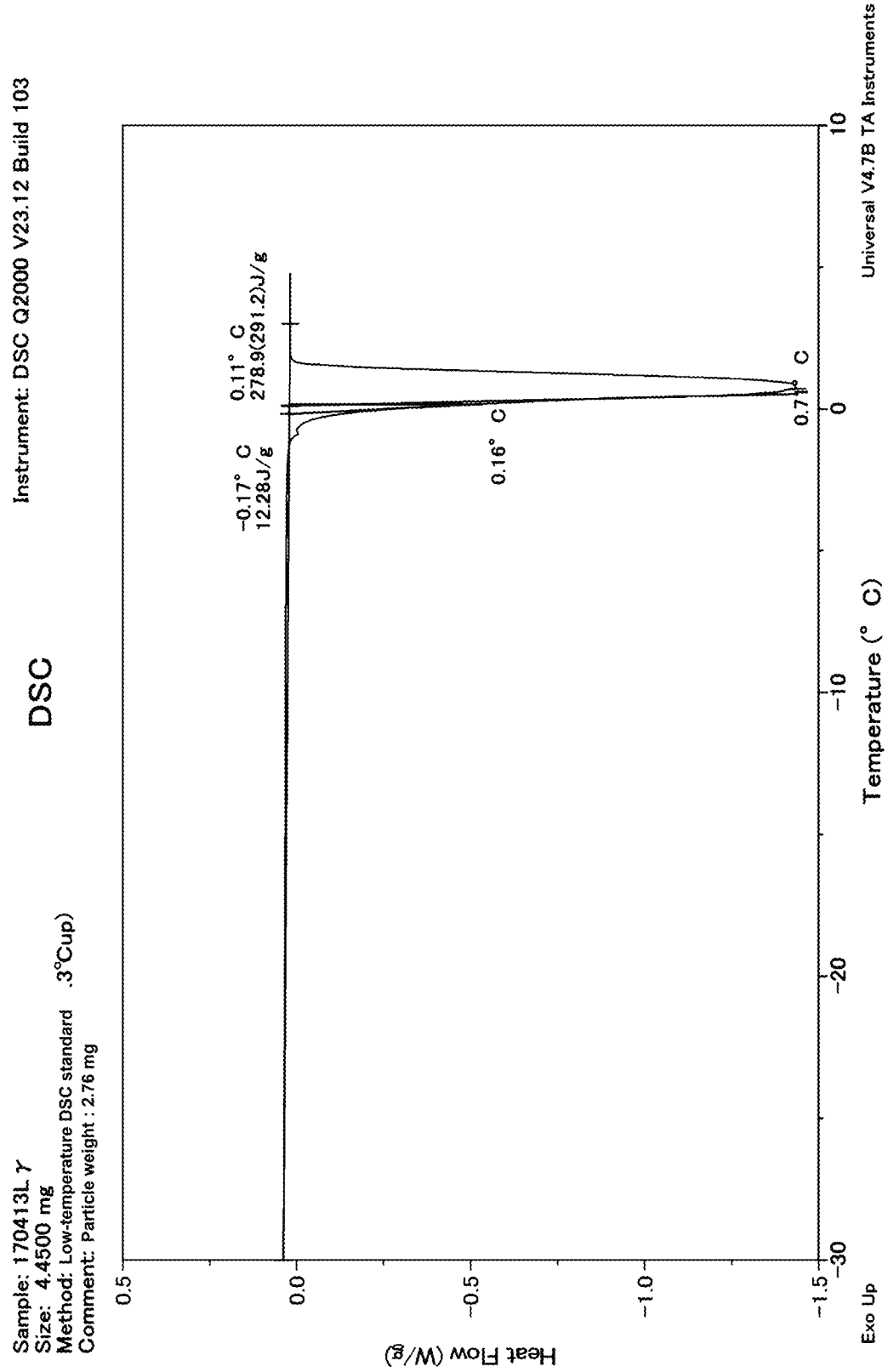
FIG. 2 is one example of DSC measurement results of a porous formed article.

<Procedures>
1. The weight of an empty pan is measured.
2. The porous formed article allowed to contain water is placed in the pan, which is then hermetically sealed, followed by the weight measurement of the pan.
3. DSC measurement is performed.
4. After the DSC measurement, a small hole is made in the hermetically sealed pan, which is then dried in vacuum at 80° C. for 8 hours or longer.
5. The weight of the pan thus dried in vacuum as described in 4 is measured.
6. The weight of the empty pan described in 1 is subtracted from the weight of the pan dried in vacuum as described in 5 to calculate the "dry weight of the porous formed article".
7. The weight of the pan dried in vacuum as described in 5 is subtracted from the weight of the pan described in 2 to calculate the total water content of the porous formed article.
8. A heat flow (on the ordinate of a graph) after the DSC measurement is normalized with the total water content.
9. In an absorption (endothermic) peak area of the DSC measurement (see FIG. 2), a zone of 0.18° C. or higher is defined as the quantity of heat of bulk water fusion (the total quantity of heat of fusion), and a zone of lower than 0.18° C. is defined as the quantity of heat of low-melting point water fusion.
10. The total water content is multiplied by a low-melting point water ratio (quantity of heat of low-melting point water fusion/total quantity of heat of fusion) obtained by DSC to calculate the "low-melting point water content".
11. The "low-melting point water content" is divided by the "dry weight of the porous formed article" to calculate the "low-melting point water content per 1 g dry weight".

The measurement described above was performed ten times, and an average value of 8 values excluding the largest and smallest values was used. The measurement equipment used is as follows.

<Equipment Used>
Apparatus: DSC Q2000 manufactured by TA Instruments, Inc. or an apparatus equivalent thereto
Atmosphere: nitrogen (flow rate: 50 mL/min.)
Temperature calibration: cyclohexane, 6.71° C.
Heat quantity calibration: cyclohexane, 31.9 J/g
Measurement cell: Tzero Hermetic AI Pan (hermetically sealed pan)
Reference: empty Tzero Hermetic Al Pan (empty pan)
Measurement temperature: −40° C. to 5° C.
Temperature increase rate: 0.3° C./min (temperature decrease rate up to −30° C.: −3° C./min)
Weighing of sample: ultramicrobalance manufactured by Mettler-Toledo International Inc.

[Contact-Induced Change Rate]

The porous formed article in a wet state was added to a measuring cylinder. The measuring cylinder was mechanically tapped at least 20 or more times. When change in volume was no longer seen, the porous formed article having an apparent volume of 10 mL was measured on a scale of the measuring cylinder. This 10 mL of the porous formed article was dried at 60° C. for 3 hours, and its dry weight was measured. Another 10 mL of the porous formed article was provided and filtered by suction. The filtration by suction employed an aspirator (the suction was performed at 0.01 MPa for 5 minutes using MDA-015 manufactured by ULVAC, Inc.) and a filter paper (PHWP04700 Mixed Cellulose Ester manufactured by Merck Millipore). The whole amount of the porous formed article filtered by suction was placed in a 200 mL three-neck flask using a funnel. 100 mL of injectable water (manufactured by Otsuka Pharmaceutical Co., Ltd.) weighed with Vollpipette was added to the three-neck flask. A three-one-motor, a clamp, a stirring shaft, and a stirring blade were attached to a stand, which was then loaded to the flask. The stirring blade used was AS ONE Corp. catalog No. 1-7733-01 (PTFE, 52 mm wide, 14 mm long, and 3.2 mm thick square type). The stirring shaft was installed at the center within the three-neck flask, and the stirring blade was installed so as to jut out of the surface of water only by 3 mm. Then, the flask was stirred at 400 rpm for 1 hour with the three-one-motor. Two filter papers through which 100 mL of injectable water was filtered by suction in advance were provided. These two filter papers were dried at 60° C. for 3 hours. Their weights were measured three times, and an average value thereof was calculated. A precise balance AUW120D manufactured by Shimadzu Corp. was used in the weight measurement. After the completion of the experiment, the liquid thus stirred was filtered through the provided two filter papers. In this respect, attention was paid such that the porous formed article in the three-neck flask would not come out thereof. Then, the flask (two times) and the funnel (two times) were washed while the whole walls were wetted with 50 mL×4 of injectable water. The filter papers were dried at 80° C. for 3 hours. Their weights were measured three times, and an average value thereof was calculated. The weight of the filter was subtracted from this weight, and the obtained weight was regarded as a contact-induced changed weight. A value drawn according to the following expression was used as the contact-induced change rate (%).

> Contact-induced change rate (%)={Contact-induced changed weight/(Dry weight of the porous formed article having an apparent volume of 10 mL)}×100

The measurement described above was performed ten times, and an average value of 8 values excluding the largest and smallest values was used.

[Amount of Fine Particles]

Each sample for evaluation was measured using a particle counter (KL-04 manufactured by RION Co., Ltd.). As for measurement values, the first measurement value was discarded, and the measurement was performed three times from the second one. An average value thereof was used as a formal value.

[Amount of Platelets Attached to Porous Formed Article]

The porous formed article described above was added into a 2.5 mL laboratory column (trade name: 2.5 mL Laboratory Column, 35 μm Filter Pore Size, manufactured by MoBiTec GmbH) with the column tapped, until an area occupied thereby in the column reached 0.8 mL, to harvest a porous formed article having an apparent volume of 0.8 mL. The apparent volume of the porous formed article included the volume of the void space, and its void ratio was 32% or more and 35% or less. Subsequently, heparin sodium (Heparin Sodium Injection 50000 Units/50 mL, manufactured by Nipro Corp.) was added at a concentration of 1000 IU/L to blood collected from a healthy volunteer (the resultant is referred to as "unprocessed blood"). 4.3 mL of the unprocessed blood was mixed with 0.8 mL of the porous formed article described above in a 5 mL polypropylene (PP) tube (this tube is referred to as a "sample tube"). Also, 5.1 mL of the unprocessed blood was added alone to another 5 mL PP tube (this tube is referred to as a "blank tube"). The sample tube and the blank tube were attached onto a disc-shaped rotating body of 20 cm in diameter of ROTATOR RT-5 (manufactured by Taitec Corp.) in a radial fashion along the radius direction of the rotating body. The disc-shaped rotating body was set such that the angle of the plane of rotation was 22 degrees from the horizontal plane. The tubes were stirred by rotation at a rate of 4 rpm at 37° C. for 3 hours. The blood in the sample tube and the blank tube thus stirred by rotation was filtered through a cell strainer (Mini Cell Strainer II, 70 μm nylon mesh, manufactured by Funakoshi Co., Ltd.) (the resultants are referred to as "processed sample blood" and "processed blank blood", respectively). The platelet concentrations of the processed sample blood and the processed blank blood were measured in a microcell counter XT-1800i (manufactured by Sysmex Corp.). The amount of platelets attached to the porous formed article was calculated according to the following expression.

> Amount of platelets adsorbed (the number (hundred million) of platelets/mL of the porous formed article (beads))=(Platelet concentration (the number of platelets/mL) of the processed blank blood−Platelet concentration (the number of platelets/mL) of the processed sample blood)× 4.3 (mL)/0.8 (mL of the porous formed article (beads))/100,000,000

In this context, the same experiment was performed ten times using blood collected from different healthy volunteers. An average value of 8 amounts of platelets attached excluding the largest and smallest values was used as the amount of platelets attached to the porous formed article.

[Measurement of Amount of Albumin Adsorbed to Porous Formed Article]

The porous formed article described above was added into a 2.5 mL laboratory column (trade name: 2.5 m Laboratory Column, 35 μm Filter Pore Size, manufactured by MoBiTec GmbH) with the column tapped, until an area occupied thereby in the column reached 1.0 mL, to harvest a porous formed article having an apparent volume of 1.0 mL. The apparent volume of the porous formed article included the volume of the void space, and its void ratio was 32% or more and 35% or less. Subsequently, 1.75 g of human albumin (manufactured by FUJIFILM Wako Pure Chemical Corp.) was completely dissolved in 50 mL of phosphate-buffered saline (PBS(−), no Calcium, no Magnesium, pH 7.4, manufactured by Thermo Fisher Scientific Inc./Gibco) to prepare a 35 mg/mL human albumin solution (this solution is referred to as an "unprocessed solution"). 4.0 mL of the unprocessed solution was mixed with 1.0 mL of the porous formed article described above in a 5 mL polypropylene (PP) tube (this tube is referred to as a "sample tube"). Also, 5.0 mL of the unprocessed solution was added alone to another 5 mL PP tube (this tube is referred to as a "blank tube"). The sample tube and the blank tube were attached onto a disc-shaped rotating body of 20 cm in diameter of ROTATOR RT-50 (manufactured by Taitec Corp.) in a radial fashion along the radius direction of the rotating body. The disc-shaped rotating body was set such that the angle of the plane of rotation was 90 degrees from the horizontal plane. The tubes were stirred by rotation at a rate of 30 rpm at 37° C. for 2 hours. The solutions in the sample tube and the blank tube thus stirred by rotation were filtered through a cell strainer (Mini Cell Strainer II, 70 μm nylon mesh, manufactured by Funakoshi Co., Ltd.) (the resultants are referred to as a "processed sample solution" and a "processed blank solution", respectively). The unprocessed solution, the processed sample solution, and the processed blank solution were each diluted 10-fold with PBS(−). The absorbance at 278 nm of the solutions thus diluted 10-fold was measured using Shimadzu ultraviolet and visible spectrophotometer UV-2600 (manufactured by Shimadzu Corp.). The amount of albumin adsorbed to the porous formed article was calculated according to the following expression.

> Amount of albumin adsorbed to the porous formed article (mg/mL of the porous formed article (beads))=((Absorbance at 278 nm of the processed blank solution diluted 10-fold)−(Absorbance at 278 nm of the processed sample solution diluted 10-fold))/(Absorbance at 278 nm of the unprocessed solution diluted 10-fold)×35 (mg/mL)×4 (mL/mL of the porous formed article (beads))

The measurement described above was performed ten times, and an average value of 8 values excluding the largest and smallest values was used.

[Average Particle Size of Porous Formed Article and Average Particle Size of Inorganic Ion Adsorbent]

The average particle size of the porous formed article and the average particle size of the inorganic ion adsorbent were measured using a laser diffraction/scattering particle size distribution measurement apparatus (LA-950 (trade name) manufactured by HORIBA, Ltd.). Water was used as dispersion medium. In sample measurement using hydrous cerium oxide as the inorganic ion adsorbent, a value of cerium oxide was used as a refractive index for the measurement. Likewise, in sample measurement using hydrous zirconium oxide as the inorganic ion adsorbent, a value of zirconium oxide was used as a refractive index for the measurement.

[Amount of Phosphorus Adsorbed from Bovine Plasma]

Figure 4:
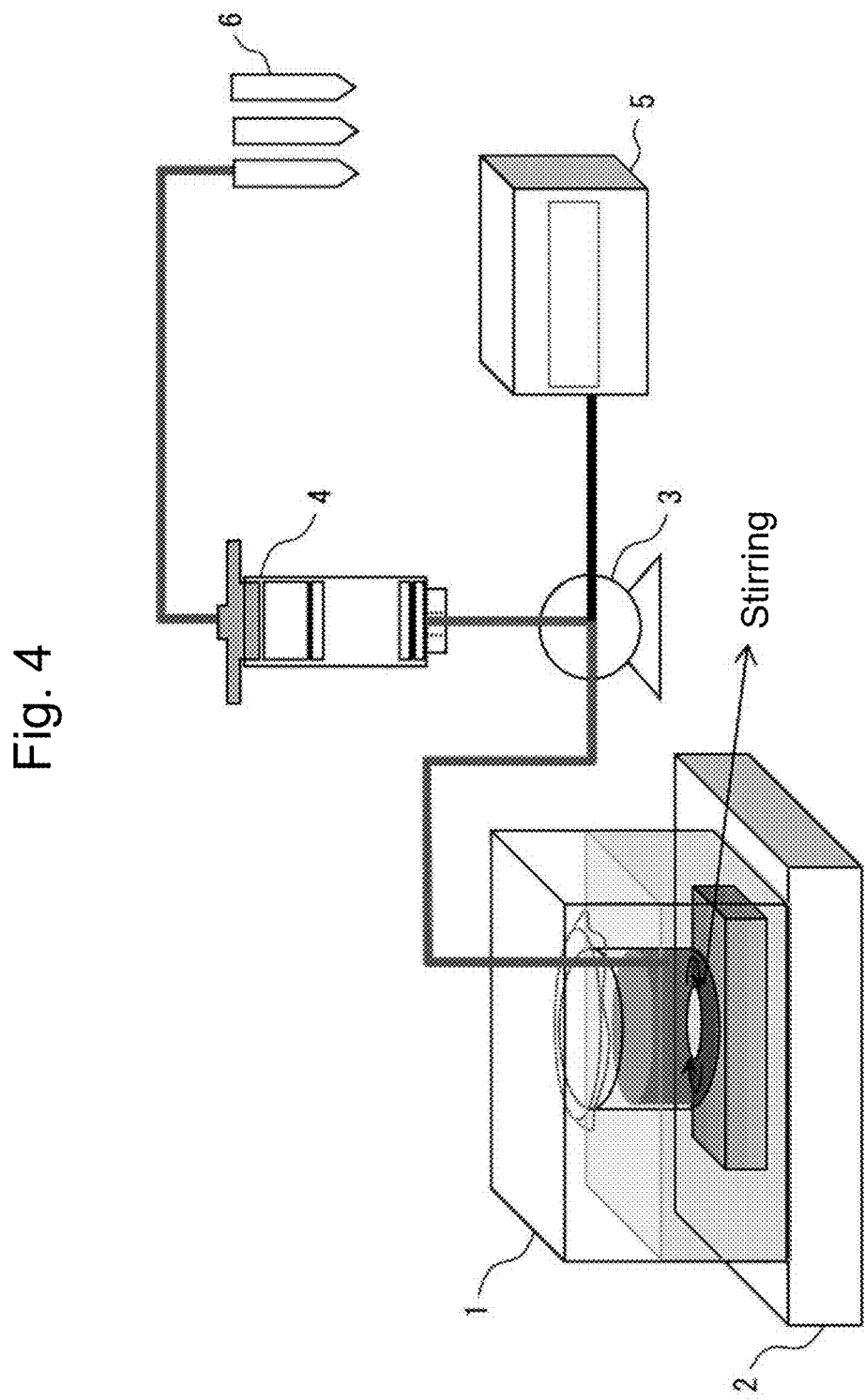
FIG. 4 is an outline diagram of a column flow test apparatus for the amount of phosphorus adsorbed to the blood purifier of the present embodiment.

The amount of phosphorus adsorbed was measured by a column flow test using low-phosphorus concentration serum from bovine plasma by use of the apparatus shown in FIG. 4. The amount of phosphorus adsorbed (mg-P/mL-Resin (porous formed article)) to the porous formed article (phosphate adsorbing agent) packed in the column was measured under conditions equivalent to general dialysis conditions (space velocity SV=120, 4-hour dialysis) using bovine plasma adjusted to a low phosphorus concentration (approximately 0.7 mg/dL).

The phosphate ion concentration was measured by the direct molybdate method.

A sample having an amount of phosphorus adsorbed of 1.5 (mg-P/mL-Resin) or larger at a passing rate of SV120 was assessed as being a favorable phosphorus binder having a large adsorption capacity.

[Presence or Absence of Hemolysis]

The amount of phosphorus adsorbed was measured by a column flow test using human blood by use of the apparatus shown in FIG. 4. A column (inside diameter: 10 mm) was packed with 8 mL of the porous formed article weighed by repetitive tapping using a measuring cylinder. Human blood (fresh human blood within 3 hours after blood collection supplemented with an anticoagulant, hematocrit value: 40 to 46%) was passed through the column by one pass at a rate of 960 mL/hr (SV120 hr-1). Discharged blood (processed blood) from the column was sampled three times every 2 minutes. The three discharged blood samples were subjected to a hemolysis test by the following method, and hemolysis was assessed as being present if even one sample had hemolysis.

(Hemolysis Test Method)

Human blood before and after filtration was centrifuged at 3000 rpm (1700×g) for 15 minutes. Then, the coloration of a supernatant portion was observed with a white sheet or the like used as a background, and compared between before and after filtration, followed by evaluation according to the following evaluation criteria.

Hemolysis present: (i) the red color of the supernatant of the blood preparation after filtration was evidently darker than that of the supernatant of the blood preparation before filtration, or (ii) the supernatant of the blood preparation after filtration was colored red as compared with the supernatant of the blood preparation before filtration.

Hemolysis absent: (iii) the supernatant of the blood preparation after filtration was not colored red as compared with the supernatant of the blood preparation before filtration.

Example 1-1

[Synthesis of Hydrophilic Polymer (Biocompatible Polymer)]

A copolymer of 2-hydroxyethyl methacrylate (HEMA) and N-methacryloyloxyethyl-N,N-dimethylammonium-α-N-methylcarboxybetaine (CMB) was synthesized by usual solution polymerization. The polymerization conditions involved performing polymerization reaction with each monomer concentration of 1 mol/L at a reaction temperature of 60° C. for 8 hours in the presence of 0.0025 mol/L azoisobutyronitrile (AIBN) as an initiator in an ethanol solution to obtain a polymer solution. The obtained polymer solution was added dropwise to diethyl ether, and a precipitated polymer was recovered. The recovered polymer was purified by reprecipitation operation using diethyl ether. Then, the obtained polymer was dried for 24 hours under a reduced pressure condition to obtain a hydrophilic polymer (biocompatible polymer).

The molar ratio between the HEMA monomeric unit and the CMB monomeric unit in the hydrophilic polymer (biocompatible polymer) was measured as follows: the obtained hydrophilic polymer (biocompatible polymer) was dissolved in dimethyl sulfoxide, followed by $^1$H-NMR measurement. From the area ratios of a peak at 4.32 ppm (derived from H atoms unique to CMB) and of 0.65 to 2.15 ppm (the total amount of H atoms) in the chart thus calculated, the molar ratio was calculated according to the following expressions.

Molar ratio of the CMB monomer=("Area ratio of the 4.32ppm region"/2)/("Area ratio of the 0.65-2.15ppm region"/5)×100

Molar ratio of the HEMA monomer=100−Molar ratio of the CMB monomer

The molar ratio between the HEMA monomeric unit and the CMB monomeric unit in the hydrophilic polymer (biocompatible polymer) was calculated as 65:35.

[Preparation of Coating Solution]

The hydrophilic polymer (biocompatible polymer) was added to 70 W/W % ethyl alcohol. Then, the mixture was stirred for 12 hours to prepare a coating solution having a hydrophilic polymer concentration of 0.1% by weight.

[Preparation of Hydrophobic Polymer]

Figure 3:
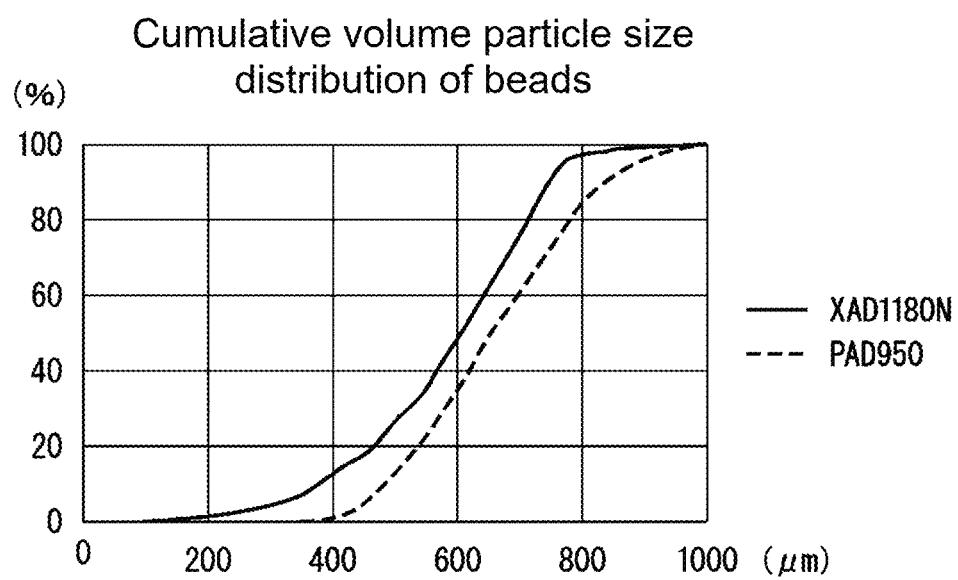
FIG. 3 is a graph of the cumulative area particle size distribution of Amberlite™ XAD™ 1180N.

The hydrophobic polymer used was Amberlite™ XAD™ 1180N (manufactured by Organo Corp., styrene polymer beads, area-average particle size: 540 μm, cumulative pore volume at pore diameters of 5 nm to 100 nm: 1.57 cm$^3$/g, cumulative pore volume at pore diameters of 100 nm to 200 nm: 0.020 cm$^3$/g). A graph of the Log differential pore volume distribution and cumulative pore volume of Amberlite™ XAD™ 1180N is shown in FIG. 1, and a graph of the cumulative area particle size distribution thereof is shown in FIG. 3.

[Production of Porous Formed Article]

[Method for Coating Hydrophobic Polymer with Hydrophilic Polymer]

3 L of Amberlite™ XAD™ 1180N swollen with ultrapure water, and 1 L of the coating solution were placed in a 5 L beaker and gently stirred for 12 hours to coat the beads with the polymer. Subsequently, the solution after the coating treatment was removed, and the obtained beads were subjected to classification and washing operations using Beads Sepa Wash (mesh opening: 328 μm, manufactured by Nippon Coke & Engineering. Co., Ltd.) to obtain coated beads having an area-average particle size of 540 μm.

[Washing with Supercritical Fluid]

The obtained porous formed article (coated beads) was washed with a supercritical fluid consisting of carbon dioxide (critical temperature: 304.1 K, critical pressure: 7.38 MPa, equipment manufactured by ITEC Co., Ltd.) for 1 hour.

[Cytokine Adsorption Performance and HMGB-1 Adsorption Performance of Porous Formed Article]

Heparin sodium (Heparin Sodium Injection 50000 Units/50 mL, manufactured by Nipro Corp.) was added at a concentration of 2000 IU/mL to blood collected from a healthy volunteer, and then, *Escherichia coli* O111:B4-derived lipopolysaccharide (LPS) (manufactured by Sigma-Aldrich Co., LLC) was added thereto at a concentration of 0.1 μg/mL. The mixture was shaken using a shaker (In Vitro Shaker WAVE-S1, manufactured by TAITEC Corp.) with a shaking angle of 10 degrees at 10 r/min at 37° C. for 24 hours. Then, the mixture was centrifuged at 2,000 g at room temperature for 20 minutes using a centrifuge (Hybrid High-Speed Refrigerated Centrifuge 6200, manufactured by KUBOTA Corp.), and the supernatant was obtained as a plasma sample. 3.6 mL of the obtained plasma sample and 0.45 mL (dry weight: 0.10 g) of the porous formed article (beads) described above were mixed in a 5 mL polypropylene (PP) tube. This tube was shaken using a shaker with a shaking angle of 10 degrees at 10 r/min at 37° C. for 2 hours (the resultant is referred to as a "sample contacted with the porous formed article (beads)"). In this respect, a sample was also provided from 3.6 mL of the obtained plasma sample without the addition of the porous formed article (beads) and subjected to the same processing as in the sample contacted with the porous formed article (beads) (the resultant is referred to as a "sample without contact with the porous formed article (beads)"). The PP tubes thus shaken were centrifuged at 2000 g at room temperature for 1 minute using a centrifuge to obtain supernatants from the sample contacted with the porous formed article (beads) and the sample without contact with the porous formed article (beads). The obtained supernatants were used in the concentration measurement of various cytokines using Bio-Plex system (Bio-Plex Pro Human Cytokine GI27-plex Panel manufactured by Bio-Rad Laboratories, Inc.) according to the attached instruction manual. Also, the HMGB-1 concentration was measured using HMGB1 ELISAK Kit II (manufactured by Shino-Test Corp.) according to the attached instruction manual. In this context, the cytokine and HMGB-1 adsorption rates of the beads were calculated according to the following expressions.

>Adsorption rate for each cytokine (%)=("Cytokine concentration of the sample without contact with the porous formed article(beads)"–"Cytokine concentration of the sample contacted with the porous formed article(beads)")/"Cytokine concentration of the sample without contact with the porous formed article(beads)"×100

>HMGB-1adsorption rate (%)=("HMGB-1concentration of the sample without contact with the porous formed article(beads)"–"HMGB-1concentration of the sample contacted with the porous formed article(beads)")/"HMGB-1concentration of the sample without contact with the beads"×100

The cytokine concentration without contact with the porous formed article (beads) and the HMGB-1 concentration without contact with the porous formed article (beads) in this experiment were IL-1b: 3658 pg/mL, IL-6: 5540 pg/mL, IL-8: 6144 pg/mL, IL-10: 846 pg/mL, TNF-α: 8085 pg/mL, and HMGB-1: 27 ng/mL.

[Preparation of Blood Purifier]

A cylindrical vessel (equipped with a glass filter at the bottom) having L/D of 1.80 and having a blood inlet and outlet was packed with the porous formed article (coated beads) swollen with degassed water, while degassed water was appropriately added thereto so as not to mingle air thereinto. The vessel thus packed was covered with a lid and joined together. Apparent volume V of the region occupied by the porous formed article was 350 mL. After packing of the vessel with the beads to the top, a vibrator was put on the side of the vessel body and moved upward and downward for 2 minutes while the body was slowly rotated. A newly formed space was further packed with the coated beads to prepare a column densely packed with the beads. Finally, the obtained column was irradiated with γ ray at 25 Kgy.

The performance of the obtained porous formed article and blood purifier is shown in Table 1 below. The low-melting point water content per 1 g dry weight of the porous formed article was 1.85 g. The contact-induced change rate of the obtained porous formed article was 0.1%, and the amount of platelets attached thereto was 230,000,000 platelets/mL. The adsorption rates were as favorable as 50% or more for cytokines except for TNF-α, 62% for TNF-α, and 65% for HMGB1. The pressure loss of the obtained blood purifier before blood processing was 7.1 kPa, and the pressure loss thereof after blood processing was 8.8 kPa. For the obtained blood purifier, 1 week, 3 months and 6 months after encapsulation of an injectable saline solution in the blood purifier, the number of 10 μm or larger fine particles in 1 mL of the saline solution was 6, 8 and 9, respectively, all of which were 25 or less. In addition, 1 week, 3 months and 6 months after encapsulation of an injectable saline solution in the blood purifier, the number of 25 μm or larger fine particles in 1 mL of the saline solution was 1, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-2

A globular porous formed article was obtained in the same way as in Example 1-1 except that a copolymer of lauryl methacrylate (LMA), N,N-diethylaminoethyl methacrylate (DEAEMA) and N-methacryloyloxyethyl-N,N-dimethylammonium-α-N-methylcarboxybetaine (CMB) was used in [Synthesis of hydrophilic polymer (biocompatible polymer)]. Also, a blood purifier was prepared in the same way as in Example 1-1.

The molar ratio among the LMA monomeric unit, the DEAEMA monomeric unit, and the CMB monomeric unit in the hydrophilic polymer (biocompatible polymer) was measured as follows: the obtained hydrophilic polymer was dissolved in dimethyl sulfoxide, followed by $^1$H-NMR measurement. From the area ratios of a peak at 4.32 ppm (derived from H atoms unique to CMB) and a peak at 2.63 ppm (derived from H atoms unique to DEAEMA), and of 0.65 to 2.15 ppm (the total amount of H atoms) in the chart thus calculated, the molar ratio was calculated according to the following expressions.

>Molar ratio of the DEAEMA monomer=("Area ratio of the 2.63ppm region"/2)/("Area ratio of the 0.65-2.15ppm region"/5–"Area ratio of 2.63ppm region"×0.3)×100

>Molar ratio of the CMB monomer=("Area ratio of the 4.32ppm region"/2)/("Area ratio of the 0.65-2.15ppm region"/5–"Area ratio of the 2.63ppm region"×0.3)×100

>Molar ratio of the LMA monomer=100–Molar ratio of the DEAEMA monomer–Molar ratio of the CMB monomer The molar ratio among the LMA monomeric unit, the DEAEMA monomeric unit, and the CMB monomeric unit in the hydrophilic polymer (biocompatible polymer) was calculated as 75/15/10.

The performance of the obtained porous formed article and blood purifier is shown in Table 1 below. The low-melting point water content per 1 g dry weight of the porous formed article was 0.15 g. The contact-induced change rate of the obtained porous formed article was 0%, and the amount of platelets attached thereto was 390,000,000 platelets/mL. The adsorption rates were as favorable as 50% or more for cytokines except for TNF-α, 85% for TNF-α, and 76% for HMGB1. The pressure loss of the obtained blood purifier before blood processing was 7.1 kPa, and the pressure loss thereof after blood processing was 12.5 kPa. For the obtained blood purifier, 1 week, 3 months and 6 months after encapsulation of an injectable saline solution in the blood purifier, the number of 10 μm or larger fine particles in 1 mL of the saline solution was 8, 9 and 10, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-3

A globular porous formed article was obtained in the same way as in Example 1-2 except that: a copolymer of lauryl methacrylate (LMA), N,N-diethylaminoethyl methacrylate (DEAEMA) and N-methacryloyloxyethyl-N,N-dimethylammonium-α-N-methylcarboxybetaine (CMB) was used in [Synthesis of hydrophilic polymer (biocompatible polymer)]; and 100 W/W % n-butyl alcohol was used instead of 70 W/W % ethyl alcohol as the solution for the hydrophilic polymer. Also, a blood purifier was prepared in the same way as in Example 1-1.

The molar ratio among the LMA monomeric unit, the DEAEMA monomeric unit, and the CMB monomeric unit in the hydrophilic polymer (biocompatible polymer) was calculated as 65/15/20.

The performance of the obtained porous formed article and blood purifier is shown in Table 1 below. The low-melting point water content per 1 g dry weight of the porous formed article was 0.70 g. The contact-induced change rate of the obtained porous formed article was 0%, and the amount of platelets attached thereto was 350,000,000 platelets/mL. The adsorption rates were as favorable as 50% or more for cytokines except for TNF-α, 70% for TNF-α, and 78% for HMGB1. The pressure loss of the obtained blood purifier before blood processing was 7.1 kPa, and the pressure loss thereof after blood processing was 12.0 kPa. For the obtained blood purifier, 1 week, 3 months and 6 months after encapsulation of an injectable saline solution in the blood purifier, the number of 10 μm or larger fine particles in 1 mL of the saline solution was 7, 8 and 10, respectively, all of which were 25 or less. In addition, 1 week, 3 months and 6 months after encapsulation of an injectable saline solution in the blood purifier, the number of 25 μm or larger fine particles in 1 mL of the saline solution was 0, 0 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-4

A globular porous formed article was obtained in the same way as in Example 1-1 except that a copolymer of 2-methoxyethyl methacrylate (MEMA) and N-methacryloyloxyethyl-N,N-dimethylammonium-α-N-methylcarboxybetaine (CMB) was used in [Synthesis of hydrophilic polymer (biocompatible polymer)]. Also, a blood purifier was prepared in the same way as in Example 1-1. The molar ratio between the MEMA monomeric unit and the CMB monomeric unit in the hydrophilic polymer (biocompatible polymer) was calculated as 73:27.

The performance of the obtained porous formed article and blood purifier is shown in Table 1 below. The low-melting point water content per 1 g dry weight of the porous formed article was 1.20 g. The contact-induced change rate of the obtained porous formed article was 0%, and the amount of platelets attached thereto was 290,000,000 platelets/mL. The adsorption rates were as favorable as 50% or more for cytokines except for TNF-α, 66% for TNF-α, and 80% for HMGB1. The pressure loss of the obtained blood purifier before blood processing was 7.1 kPa, and the pressure loss thereof after blood processing was 10.5 kPa. For the obtained blood purifier, 1 week, 3 months and 6 months after encapsulation of an injectable saline solution in the blood purifier, the number of 10 μm or larger fine particles in 1 mL of the saline solution was 6, 6 and 9, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Comparative Example 1-1

In [Synthesis of hydrophilic polymer (biocompatible polymer)], 7.50 g of 3-methoxypropyl acrylate (MC3A), 30.2 g of 1,4-dioxane, and 7.5 mg of azobisisobutyronitrile (AIBN) were added to a three-neck eggplant flask. The reaction solution was stirred for 30 minutes while dry nitrogen gas was injected thereto, to purge the reaction system with nitrogen. The three-neck eggplant flask was immersed in an oil bath with its lower part temperature set to 75° C., and stirred for 6 hours under nitrogen stream to perform polymerization. The progression of the polymerization reaction was confirmed by $^1$H NMR. After confirmation of a sufficiently high rate of conversion (around 90%) of the reaction, the polymerization system was allowed to cool to room temperature to terminate the reaction. The polymerization solution was added dropwise to hexane to precipitate the polymer. The supernatant was removed by decanting, and the precipitates were dissolved in tetrahydrofuran for recovery. The polymer was purified by two repetitive operations of dissolution in tetrahydrofuran followed by reprecipitation in hexane. The obtained precipitates were further stirred for 24 hours in water. Water was removed by decanting, and the precipitates were dissolved in tetrahydrofuran for recovery. The solvent was distilled off under reduced pressure. Then, the residue was dried in a vacuum dryer to obtain the polymer. A molecular weight was measured using a portion of the obtained polymer and was consequently a number-average molecular weight (Mn) of 31000 and a molecular weight distribution (Mw/Mn) of 2.5.

The performance of the obtained porous formed article and blood purifier is shown in Table 1 below. The low-melting point water content per 1 g dry weight of the porous formed article was 0.10 g. The contact-induced change rate of the obtained porous formed article was 0%, and the amount of platelets attached thereto was 420,000,000 platelets/mL. The adsorption rate for IL-6 and IL-10 among cytokines except for TNF-α was less than 50%. The amount of platelets attached, the pressure loss of the blood purifier before blood processing, and the adsorption rate for cytokines except for TNF-α produced unfavorable results.

Comparative Example 1-2

A globular porous formed article was obtained in the same way as in Example 1-1 except that a copolymer of 2-hydroxyethyl methacrylate (HEMA) and N-methacryloyloxyethyl-N,N-dimethylammonium-α-N-methylcarboxybetaine (CMB) was used in [Synthesis of hydrophilic polymer (biocompatible polymer)]. Also, a blood purifier was prepared in the same way as in Example 1-1. The molar ratio between the HEMA monomeric unit and the CMB monomeric unit in the hydrophilic polymer (biocompatible polymer) was calculated as 58:42.

The performance of the obtained porous formed article and blood purifier is shown in Table 1 below. The low-melting point water content per 1 g dry weight of the porous formed article was 2.20 g. The contact-induced change rate of the obtained porous formed article was 0.2%, and the amount of platelets attached thereto was 100,000,000 platelets/mL. The adsorption rate for cytokines except for TNF-α was as favorable as 50% or more, whereas the TNF-α adsorption rate and the HMGB1 adsorption rate produced unfavorable results (24% and 53%, respectively).

Example 1-5

A globular porous formed article was obtained in the same way as in Example 1-1 except that a copolymer of 2-hydroxyethyl methacrylate (HEMA) and N-methacryloyloxyethyl-N,N-dimethylammonium-α-N-methylcarboxybetaine (CMB) was used in [Synthesis of hydrophilic polymer (biocompatible polymer)]. Also, a blood purifier was prepared in the same way as in Example 1-1. The molar ratio between the HEMA monomeric unit and the CMB monomeric unit in the hydrophilic polymer (biocompatible polymer) was calculated as 60:40.

The performance of the obtained porous formed article and blood purifier is shown in Table 1 below. The low-melting point water content per 1 g dry weight of the porous formed article was 1.95 g. The contact-induced change rate of the obtained porous formed article was 0.2%, and the amount of platelets attached thereto was 150,000,000 platelets/mL. The adsorption rates were as favorable as 50% or more for cytokines except for TNF-α, 35% for TNF-α, and 60% for HMGB1. The pressure loss of the obtained blood purifier before blood processing was 7.1 kPa, and the pressure loss thereof after blood processing was 7.6 kPa. For the obtained blood purifier, 1 week, 3 months and 6 months after encapsulation of an injectable saline solution in the blood purifier, the number of 10 μm or larger fine particles in 1 mL of the saline solution was 5, 6 and 7, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-6

The same operation as in Example 1-1 was performed except that L/D of the cylindrical vessel (equipped with a glass filter at the bottom) having a blood inlet and outlet was 1.20 in [Preparation of blood purifier].

The performance of the obtained porous formed article and blood purifier is shown in Table 1 below. The low-melting point water content per 1 g dry weight of the porous formed article was 1.85 g. The contact-induced change rate of the obtained porous formed article was 0.1%, and the amount of platelets attached thereto was 230,000,000 platelets/mL. The adsorption rates were as favorable as 50% or more for cytokines except for TNF-α, 62% for TNF-α, and 65% for HMGB1. The pressure loss of the obtained blood purifier before blood processing was 4.1 kPa, and the pressure loss thereof after blood processing was 4.3 kPa. For the obtained blood purifier, 1 week, 3 months and 6 months after encapsulation of an injectable saline solution in the blood purifier, the number of 10 μm or larger fine particles in 1 mL of the saline solution was 5, 6 and 8, respectively, all of which were 25 or less. In addition, 1 week, 3 months and 6 months after encapsulation of an injectable saline solution in the blood purifier, the number of 25 μm or larger fine particles in 1 mL of the saline solution was 1, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-7

The same operation as in Example 1-1 was performed except that L/D of the cylindrical vessel (equipped with a glass filter at the bottom) having a blood inlet and outlet was 2.20 in [Preparation of blood purifier].

The performance of the obtained porous formed article and blood purifier is shown in Table 2 below. The low-melting point water content per 1 g dry weight of the porous formed article was 1.85 g. The contact-induced change rate of the obtained porous formed article was 0.1%, and the amount of platelets attached thereto was 230,000,000 platelets/mL. The adsorption rates were as favorable as 50% or more for cytokines except for TNF-α, 62% for TNF-α, and 65% for HMGB1. The pressure loss of the obtained blood purifier before blood processing was 9.3 kPa, and the pressure loss thereof after blood processing was 12.5 kPa. For the obtained blood purifier, 1 week, 3 months and 6 months after encapsulation of an injectable saline solution in the blood purifier, the number of 10 µm or larger fine particles in 1 mL of the saline solution was 5, 6 and 7, respectively, all of which were 25 or less. In addition, 1 week, 3 months and 6 months after encapsulation of an injectable saline solution in the blood purifier, the number of 25 µm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Comparative Example 1-3

The same operation as in Example 1-1 was performed except that L/D of the cylindrical vessel (equipped with a glass filter at the bottom) having a blood inlet and outlet was 2.40 in
[Preparation of Blood Purifier].

The performance of the obtained porous formed article and blood purifier is shown in Table 2 below. The low-melting point water content per 1 g dry weight of the porous formed article was 1.85 g. The contact-induced change rate of the obtained porous formed article was 0.1%, and the amount of platelets attached thereto was 230,000,000 platelets/mL. The adsorption rates were as favorable as 50% or more for cytokines except for TNF-α, 62% for TNF-α, and 65% for HMGB1. The pressure loss of the obtained blood purifier before and after blood processing produced unfavorable results (10.5 kPa and 13.5 kPa, respectively).

Comparative Example 1-4

The same operation as in Example 1-7 was performed except that a hydrophilic polymer Purosorb™ PAD950 (manufactured by Purolite Corp. acrylic polymer beads, area-average particle size: 621 µm, cumulative pore volume at pore diameters of 5 nm to 100 nm: 0.823 cm³/g, cumulative pore volume at pore diameters of 100 nm to 200 nm: 0.038 cm³/g) was used instead of the hydrophobic polymer Amberlite™ XAD™ 1180N in [Preparation of hydrophobic polymer].

The performance of the obtained porous formed article and blood purifier is shown in Table 2 below. The low-melting point water content per 1 g dry weight of the porous formed article was 1.85 g. The contact-induced change rate of the obtained porous formed article produced unfavorable results of 0.3%. The unfavorable contact-induced change rate is probably in part because the porous formed article before coating with the hydrophilic polymer was fragile beads and was not the hydrophobic polymer.

Example 1-8

[Production of Porous Formed Article]

A globular porous formed article containing polyetherimide (PEI) and polyvinylpyrrolidone (PVP) was prepared by the following procedures and used.

2000 g of cerium sulfate tetrahydrate (Wako Pure Chemical Industries, Ltd.) was added into 50 L of pure water and dissolved using a stirring blade. Then, 3 L of 8 M caustic soda (Wako Pure Chemical Industries, Ltd.) was added dropwise thereto at a rate of 20 ml/min to obtain hydrous cerium oxide precipitates. The obtained precipitates were filtered with a filter press and then washed by passing therethrough 500 L of pure water. Further, 80 L of ethanol (Wako Pure Chemical Industries, Ltd.) was passed therethrough to replace moisture contained in the hydrous cerium oxide with ethanol. In this respect, 10 ml of the filtrate at the completion of filtration was collected, and the moisture percentage was measured using in a Karl Fischer moisture percentage meter (CA-200 (trade name) manufactured by Mitsubishi Chemical Analytech Co., Ltd.). As a result, the moisture percentage was 5% by mass, and the replacement rate with the organic liquid was 95% by mass. The obtained hydrous cerium oxide containing the organic liquid was dried in air to obtain dried hydrous cerium oxide. The obtained dried hydrous cerium oxide was milled using a jet mill apparatus (SJ-100 (trade name) manufactured by Nisshin Engineering Inc.) under conditions involving a pneumatic pressure of 0.8 MPa and a raw material feed rate of 100 g/hr to obtain a hydrous cerium oxide powder having an average particle size of 1.2 µm.

220 g of N-methyl-2-pyrrolidone (NMP, manufactured by Mitsubishi Chemical Corp.), 120 g of the milled hydrous cerium oxide powder (MOX), 28 g of polyetherimide (PEI, GENERAL ELECTRIC Co., Ultem 1010) as the hydrophobic polymer, and 32 g of polyvinylpyrrolidone (PVP, K90 manufactured by BASF SE, weight-average molecular weight: 1,200,000) as the hydrophilic polymer were added, warmed to 60° C. in a dissolution vessel, and stirred and dissolved using a stirring blade to obtain a homogeneous slurry solution for shaping.

The obtained slurry for shaping was supplied to the inside of a cylindrical rotary container in which a nozzle having a diameter of 4 mm was opened on the side. This container was rotated to form liquid droplets from the nozzle through centrifugal force (15 G). The liquid droplets were allowed to arrive at a coagulating liquid (content of NMP with respect to water: 50% by mass) warmed to 60° C., which was retained in a coagulation vessel having an upper opening, to coagulate the slurry for shaping. After ethanol replacement, alkali washing and classification were further performed to obtain a globular porous formed article containing polyetherimide (PEI) and polyvinylpyrrolidone (PVP). The particle size of the porous formed article was 537 µm.
[Washing with Supercritical Fluid]

The obtained porous formed article was washed with a supercritical fluid consisting of carbon dioxide (critical temperature: 304.1 K, critical pressure: 7.38 MPa, equipment manufactured by ITEC Co., Ltd.) for 1 hour. This operation was repetitively performed twice.
[PMEA Coating]

A cylindrical vessel (equipped with a glass filter at the bottom) having L/D of 1.80 and having a blood inlet and outlet was packed with the obtained porous formed article.

Apparent volume V of the region occupied by the porous formed article was 350 mL. Subsequently, 0.2 g of PMEA (Mn: 20,000, Mw/Mn: 2.4) was dissolved in an aqueous solution (100 g) of 45 g of methanol/55 g of water to prepare a coating solution. The vessel packed with the porous formed article was vertically held, and the coating solution was injected from above at a flow rate of 100 mL/min so that the coating solution was contacted with the porous formed article, which was then washed with pure water. After the washing with pure water, the coating solution in the vessel was blown off with 0.1 KMpa of air. The module was placed in a vacuum dryer, dried in vacuum at 35° C. for 15 hours, and sterilized with gamma ray at 25 Kgy in the atmosphere to prepare a blood purifier similar to that of Example 1-1.

The performance of the obtained porous formed article and blood purifier is shown in Table 2 below. The low-melting point water content per 1 g dry weight of the porous formed article was 0.62 g. The contact-induced change rate of the obtained porous formed article was 0.2%, and the amount of platelets attached thereto was 360,000,000 platelets/mL. The adsorption rates were as favorable as 50% or more for cytokines except for TNF-α, 30% for TNF-α, and 95% for HMGB1. The pressure loss of the obtained blood purifier before blood processing was 7.2 kPa, and the pressure loss thereof after blood processing was 12.0 kPa. For the obtained blood purifier, 1 week, 3 months and 6 months after encapsulation of an injectable saline solution in the blood purifier, the number of 10 μm or larger fine particles in 1 mL of the saline solution was 2, 4 and 6, respectively, all of which were 25 or less. In addition, 1 week, 3 months and 6 months after encapsulation of an injectable saline solution in the blood purifier, the number of 25 μm or larger fine particles in 1 mL of the saline solution was 1, 1 and 2, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-9

A blood purifier was prepared in the same way as in Example 1-8 except that in [Production of porous formed article], 217.6 g of N-methyl-2-pyrrolidone (NMP, manufactured by Mitsubishi Chemical Corp.) NMP as the good solvent for hydrophobic polymers, 31.6 g of polyvinylpyrrolidone (PVP, K90 manufactured by BASF SE, weight-average molecular weight: 1,200,000) as the hydrophilic polymer, 119.2 g of lanthanum oxide (manufactured by Nacalai Tesque, Inc.) instead of MOX, and 31.6 g of polyethersulfone (PES, manufactured by Sumitomo Chemical Co., Ltd.) as the hydrophobic polymer were used to obtain a globular porous formed article containing polyvinylpyrrolidone (PVP) and polyethersulfone (PES).

The performance of the obtained blood purifier is shown in Table 2 below. The blood purifier had high ability to adsorb phosphorus, was free from hemolysis, and was safely usable with the number of fine particles satisfying the Approval Standards for Artificial Kidney Apparatus. The low-melting point water content per 1 g dry weight of the porous formed article was 0.62 g. The contact-induced change rate of the obtained porous formed article was 0.2%, and the amount of platelets attached thereto was 360,000,000 platelets/mL. The adsorption rates were as favorable as 50% or more for cytokines except for TNF-α, 38% for TNF-α, and 95% for HMGB1. The pressure loss of the obtained blood purifier before blood processing was 7.3 kPa, and the pressure loss thereof after blood processing was 12.2 kPa. For the obtained blood purifier, 1 week, 3 months and 6 months after encapsulation of an injectable saline solution in the blood purifier, the number of 10 μm or larger fine particles in 1 mL of the saline solution was 6, 7 and 10, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 2, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-10

A blood purifier was prepared in the same way as in Example 1-9 except that in [Production of porous formed article], polysulfone (PSf, P-1700 manufactured by Amco Engineering Polymers) as the hydrophobic polymer was used to obtain a globular porous formed article containing polysulfone (PSf) and polyvinylpyrrolidone (PVP).

The performance of the obtained porous formed article and blood purifier is shown in Table 2 below. The low-melting point water content per 1 g dry weight of the porous formed article was 0.62 g. The contact-induced change rate of the obtained porous formed article was 0.2%, and the amount of platelets attached thereto was 360,000,000 platelets/mL. The adsorption rates were as favorable as 50% or more for cytokines except for TNF-α, 40% for TNF-α, and 97% for HMGB1. The pressure loss of the obtained blood purifier before blood processing was 7.3 kPa, and the pressure loss thereof after blood processing was 12.2 kPa. For the obtained blood purifier, 1 week, 3 months and 6 months after encapsulation of an injectable saline solution in the blood purifier, the number of 10 μm or larger fine particles in 1 mL of the saline solution was 6, 8 and 10, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-11

A globular porous formed article was obtained in the same way as in Example 1-1 except that a copolymer of 2-methoxyethyl methacrylate (MEMA) and N-methacryloyloxyethyl-N,N-dimethylammonium-α-N-methylcarboxybetaine (CMB) was used in [Synthesis of hydrophilic polymer (biocompatible polymer)]. Also, a blood purifier was prepared in the same way as in Example 1-1. The molar ratio between the MEMA monomeric unit and the CMB monomeric unit in the hydrophilic polymer (biocompatible polymer) was calculated as 98:2.

The performance of the obtained porous formed article and blood purifier is shown in Table 2 below. The low-melting point water content per 1 g dry weight of the porous formed article was 0.43 g. The contact-induced change rate of the obtained porous formed article was 0%, and the amount of platelets attached thereto was 360,000,000 platelets/mL. The adsorption rates were as favorable as 50% or more for cytokines except for TNF-α, 75% for TNF-α, and 70% for HMGB1. The pressure loss of the obtained blood purifier before blood processing was 7.1 kPa, and the pressure loss thereof after blood processing was 10.8 kPa. For the obtained blood purifier, 1 week, 3 months and 6 months after encapsulation of an injectable saline solution in the blood purifier, the number of 10 μm or larger fine particles in 1 mL of the saline solution was 5, 5 and 7, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

Example 1-12

A globular porous formed article was obtained in the same way as in Example 1-1 except that a copolymer of lauryl methacrylate (LMA) and N-methacryloyloxyethyl-N,N-dimethylammonium-α-N-methylcarboxybetaine (CMB) was further used in coating in [Synthesis of hydrophilic polymer (biocompatible polymer)]. A blood purifier was prepared in the same way as in Example 1-1. The molar ratio between the LMA monomeric unit and the CMB monomeric unit was calculated as 98:2.

The performance of the obtained porous formed article and blood purifier is shown in Table 2 below. The low-melting point water content per 1 g dry weight of the porous formed article was 0.37 g. The contact-induced change rate of the obtained porous formed article was 0%, and the amount of platelets attached thereto was 370,000,000 platelets/mL. The adsorption rates were as favorable as 50% or more for cytokines except for TNF-α, 79% for TNF-α, and 72% for HMGB1. The pressure loss of the obtained blood purifier before blood processing was 7.1 kPa, and the pressure loss thereof after blood processing was 10.9 kPa. For the obtained blood purifier, 1 week, 3 months and 6 months after encapsulation of an injectable saline solution in the blood purifier, the number of 10 μm or larger fine particles in 1 mL of the saline solution was 6, 6 and 8, respectively, all of which were 25 or less. In addition, 1 week, 3 months and 6 months after encapsulation of an injectable saline solution in the blood purifier, the number of 25 μm or larger fine particles in 1 mL of the saline solution was 0, 1 and 1, respectively, all of which were 3 or less. Both the numbers of fine particles satisfied the Approval Standards for Artificial Kidney Apparatus stipulated by Ministry of Health, Labour and Welfare, Japan. In conclusion, the obtained blood purifier was a blood purifier having a porous formed article, which is excellent in blood compatibility, has favorable cytokine adsorption performance, has a low pressure loss before and after blood processing, and is safely usable with the number of fine particles satisfying the Approval Standards for Artificial Kidney Apparatus.

TABLE 1

|  | Example 1-1 | Example 1-2 | Example 1-3 | Example 1-4 |
| --- | --- | --- | --- | --- |
| Hydrophobic polymer | Styrene polymer | Styrene polymer | Styrene polymer | Styrene polymer |
| Cytokine adsorbent | Absent | Absent | Absent | Absent |
| Hydrophilic polymer | HEMA/CMB = 65/35 | LMA/DEAEMA/CMB = 75/15/10 | LMA/DEAEMA/CMB = 65/15/20 | MEMA/CMB = 73/27 |
| Low-melting point water content (g) | 1.85 | 0.15 | 0.70 | 1.20 |
| Contact-induced change rate (%) | 0.1 | 0 | 0 | 0 |
| Amount of platelets attached (the number (hundred million) of platelets/mL) | 2.3 | 3.9 | 3.5 | 2.9 |
| Pressure loss before blood processing (kPa) | 7.1 | 7.1 | 7.1 | 7.1 |
| Pressure loss after blood processing (kPa) | 8.8 | 12.5 | 12.0 | 10.5 |
| L/D | 1.80 | 1.80 | 1.80 | 1.80 |
| Apparent volume V of porous formed article (mL) | 350 | 350 | 350 | 350 |
| Area-average particle size (μm) | 540 | 540 | 540 | 540 |
| Cumulative pore volume at pore diameters of 5 nm or larger and 100 nm or smaller ($cm^3/g$) | 1.55 | 1.56 | 1.55 | 1.57 |
| Cumulative pore volume at pore diameters of 100 nm or larger and 200 nm or smaller ($cm^3/g$) | 0.021 | 0.020 | 0.021 | 0.020 |
| Amount of albumin adsorbed (mg/mL) | 62 | 63 | 63 | 63 |
| IL-1b adsorption rate (%) | 88 | 66 | 77 | 80 |
| IL-6 adsorption rate (%) | 70 | 54 | 63 | 65 |
| IL-8 adsorption rate (%) | 96 | 78 | 88 | 90 |

TABLE 1-continued

| | | | | |
|---|---|---|---|---|
| IL-10 adsorption rate (%) | 73 | 54 | 62 | 66 |
| TNF-α adsorption rate (%) | 62 | 85 | 70 | 66 |
| HMGB1 adsorption rate (%) | 65 | 76 | 78 | 80 |

| | Comparative Example 1-1 | Comparative Example 1-2 | Example 1-5 | Example 1-6 |
|---|---|---|---|---|
| Hydrophobic polymer | Styrene polymer | Styrene polymer | Styrene polymer | Styrene polymer |
| Cytokine adsorbent | Absent | Absent | Absent | Absent |
| Hydrophilic polymer | MC3A | HEMA/CMB = 58/42 | HEMA/CMB = 60/40 | HEMA/CMB = 65/35 |
| Low-melting point water content (g) | 0.10 | 2.20 | 1.95 | 1.85 |
| Contact-induced change rate (%) | 0 | 0.2 | 0.2 | 0.1 |
| Amount of platelets attached (the number (hundred million) of platelets/mL) | 4.2 | 1.0 | 1.5 | 2.3 |
| Pressure loss before blood processing (kPa) | 7.1 | 7.1 | 7.1 | 4.1 |
| Pressure loss after blood processing (kPa) | 15.0 | 7.4 | 7.6 | 4.3 |
| L/D | 1.80 | 1.80 | 1.80 | 1.20 |
| Apparent volume V of porous formed article (mL) | 350 | 350 | 350 | 350 |
| Area-average particle size (μm) | 540 | 540 | 540 | 540 |
| Cumulative pore volume at pore diameters of 5 nm or larger and 100 nm or smaller ($cm^3/g$) | 1.57 | 1.57 | 1.57 | 1.55 |
| Cumulative pore volume at pore diameters of 100 nm or larger and 200 nm or smaller ($cm^3/g$) | 0.022 | 0.020 | 0.020 | 0.021 |
| Amount of albumin adsorbed (mg/mL) | 61 | 63 | 63 | 62 |
| IL-1b adsorption rate (%) | 60 | 93 | 91 | 88 |
| IL-6 adsorption rate (%) | 49 | 75 | 73 | 70 |
| IL-8 adsorption rate (%) | 70 | 98 | 97 | 96 |
| IL-10 adsorption rate (%) | 49 | 77 | 76 | 73 |
| TNF-α adsorption rate (%) | 88 | 24 | 35 | 62 |
| HMGB1 adsorption rate (%) | 74 | 53 | 60 | 65 |

TABLE 2

| | Example 1-7 | Comparative Example 1-3 | Comparative Example 1-4 | Example 1-8 |
|---|---|---|---|---|
| Hydrophobic polymer | Styrene polymer | Styrene polymer | Absent (acrylic polymer was used) | PEI |
| Cytokine adsorbent | Absent | Absent | Absent | Hydrous cerium oxide |
| Hydrophilic polymer | HEMA/CMB = 65/35 | HEMA/CMB = 65/35 | HEMA/CMB = 65/35 | PVP & PMEA |
| Low-melting point water content (g) | 1.85 | 1.85 | 1.85 | 0.62 |
| Contact-induced change rate (%) | 0.1 | 0.1 | 0.3 | 0.2 |
| Amount of platelets attached (the number (hundred million) of platelets/mL) | 2.3 | 2.3 | 2.3 | 3.6 |
| Pressure loss before blood processing (kPa) | 9.3 | 10.5 | 9.3 | 7.2 |
| Pressure loss after blood processing (kPa) | 12.5 | 13.5 | 14.0 | 12.0 |
| L/D | 2.20 | 2.40 | 2.20 | 1.80 |
| Substantial volume of blood purifier (mL) | 350 | 350 | 350 | 350 |
| Area-average particle size (μm) | 540 | 540 | 540 | 537 |
| Cumulative pore volume at pore diameters of 5 nm or larger and 100 nm or smaller ($cm^3/g$) | 1.55 | 1.55 | 1.55 | 0.5 |
| Cumulative pore volume at pore diameters of 100 nm or larger and 200 nm or smaller ($cm^3/g$) | 0.021 | 0.021 | 0.021 | 0.020 |
| Amount of albumin adsorbed (mg/mL) | 62 | 62 | 61 | 21 |
| IL-1b adsorption rate (%) | 88 | 88 | 87 | 87 |
| IL-6 adsorption rate (%) | 70 | 70 | 70 | 66 |
| IL-8 adsorption rate (%) | 96 | 96 | 96 | 84 |
| IL-10 adsorption rate (%) | 73 | 73 | 72 | 66 |
| TNF-α adsorption rate (%) | 62 | 62 | 62 | 30 |
| HMGB1 adsorption rate (%) | 65 | 65 | 64 | 95 |

TABLE 2-continued

|  | Example 1-9 | Example 1-10 | Example 1-11 | Example 1-12 |
|---|---|---|---|---|
| Hydrophobic polymer | PES | PSf | Styrene polymer | Styrene polymer |
| Cytokine adsorbent | Hydrous cerium oxide | Hydrous cerium oxide | Absent | Absent |
| Hydrophilic polymer | PVP & PMEA | PVP & PMEA | MEMA/CMB = 98/2 | LMA/CMB = 98/2 |
| Low-melting point water content (g) | 0.62 | 0.62 | 0.43 | 0.37 |
| Contact-induced change rate (%) | 0.2 | 0.2 | 0 | 0 |
| Amount of platelets attached (the number (hundred million) of platelets/mL) | 3.6 | 3.6 | 3.6 | 3.7 |
| Pressure loss before blood processing (kPa) | 7.3 | 7.4 | 7.1 | 7.1 |
| Pressure loss after blood processing (kPa) | 12.2 | 12.4 | 10.8 | 10.9 |
| L/D | 1.80 | 1.80 | 1.80 | 1.80 |
| Substantial volume of blood purifier (mL) | 350 | 350 | 350 | 350 |
| Area-average particle size (μm) | 533 | 530 | 540 | 540 |
| Cumulative pore volume at pore diameters of 5 nm or larger and 100 nm or smaller ($cm^3/g$) | 0.55 | 0.51 | 1.55 | 1.55 |
| Cumulative pore volume at pore diameters of 100 nm or larger and 200 nm or smaller ($cm^3/g$) | 0.021 | 0.021 | 0.020 | 0.020 |
| Amount of albumin adsorbed (mg/mL) | 20 | 21 | 61 | 61 |
| IL-1b adsorption rate (%) | 95 | 93 | 73 | 72 |
| IL-6 adsorption rate (%) | 78 | 80 | 60 | 59 |
| IL-8 adsorption rate (%) | 95 | 98 | 82 | 81 |
| IL-10 adsorption rate (%) | 72 | 73 | 59 | 57 |
| TNF-α adsorption rate (%) | 38 | 40 | 75 | 79 |
| HMGB1 adsorption rate (%) | 95 | 97 | 70 | 72 |

Example 2-1

2000 g of cerium sulfate tetrahydrate (Wako Pure Chemical Industries, Ltd.) was added into 50 L of pure water and dissolved using a stirring blade. Then, 3 L of 8 M caustic soda (Wako Pure Chemical Industries, Ltd.) was added dropwise thereto at a rate of 20 ml/min to obtain hydrous cerium oxide precipitates. The obtained precipitates were filtered with a filter press and then washed by passing therethrough 500 L of pure water. Further, 80 L of ethanol (Wako Pure Chemical Industries, Ltd.) was passed therethrough to replace moisture contained in the hydrous cerium oxide with ethanol. In this respect, 10 ml of the filtrate at the completion of filtration was collected, and the moisture percentage was measured using a Karl Fischer moisture percentage meter (CA-200 (trade name) manufactured by Mitsubishi Chemical Analytech Co., Ltd.). As a result, the moisture percentage was 5% by mass, and the replacement rate with the organic liquid was 95% by mass. The obtained hydrous cerium oxide containing the organic liquid was dried in air to obtain dried hydrous cerium oxide. The obtained dried hydrous cerium oxide was milled using a jet mill apparatus (SJ-100 (trade name) manufactured by Nisshin Engineering Inc.) under conditions involving a pneumatic pressure of 0.8 MPa and a raw material feed rate of 100 g/hr to obtain a hydrous cerium oxide powder having an average particle size of 1.2 μm.

220 g of dimethyl sulfoxide (DMSO, manufactured by Kanto Chemical Co., Inc.), 120 g of the milled hydrous cerium oxide powder (MOX), 28 g of poly(methyl methacrylate) (PMMA, manufactured by Mitsubishi Chemical Corp., trade name: Dianal BR-77), and 32 g of polyvinylpyrrolidone (PVP, K90 manufactured by BASF SE) as the hydrophilic polymer (water-soluble polymer) were added, warmed to 60° C. in a dissolution vessel, and stirred and dissolved using a stirring blade to obtain a homogeneous slurry solution for shaping.

The obtained slurry for shaping was supplied to the inside of a cylindrical rotary container in which a nozzle having a diameter of 4 mm was opened on the side. This container was rotated to form liquid droplets from the nozzle through centrifugal force (15 G). The liquid droplets were allowed to arrive at a coagulating liquid (content of NMP with respect to water: 50% by mass) warmed to 60° C., which was retained in a coagulation vessel having an upper opening, to coagulate the slurry for shaping. After ethanol replacement, alkali washing and classification were further performed to obtain a globular porous formed article. The particle size of the porous formed article was 537 μm.

[Washing with Supercritical Fluid]

The obtained porous formed article was washed with a supercritical fluid consisting of carbon dioxide (critical temperature: 304.1 K, critical pressure: 7.38 MPa, equipment manufactured by ITEC Co., Ltd.) for 1 hour.

[PMEA Coating]

A cylindrical vessel (equipped with a glass filter at the bottom, L (length)/D (cylinder diameter): 1.5) was packed with 1 mL of the obtained porous formed article. Subsequently, 0.2 g of PMEA (Mn: 20,000, Mw/Mn: 2.4) was dissolved in an aqueous solution (100 g) of 40 g of methanol/60 g of water to prepare a coating solution. The vessel packed with the porous formed article was vertically held, and the coating solution was injected from above at a flow rate of 100 mL/min so that the coating solution was contacted with the porous formed article, which was then washed with pure water.

After the washing with pure water, the coating solution in the vessel was blown off with 0.1 KMpa of air. The module was placed in a vacuum dryer, dried in vacuum at 35° C. for 15 hours, and sterilized with gamma ray at 25 Kgy in the atmosphere to prepare a blood purifier.

[Column Flow Test Using Low-Phosphorus Concentration Serum from Bovine Plasma]

Assuming that a phosphate binder is used downstream of a dialyzer at the time of dialysis treatment, the amount of phosphorus adsorbed was measured at an inorganic phosphorus concentration of 0.2 to 1.0 mg/dL in blood at the outlet of a dialyzer at the time of dialysis treatment. Therefore, the phosphorus concentration of a test plasma fluid was adjusted. Commercially available bovine serum was centrifuged (3500 rpm, 5 min) to prepare 2000 mL of a supernatant plasma. The phosphorus concentration in the plasma was 10.8 mg/dL. To half (1000 mL) the amount of the obtained plasma, the porous formed article obtained in Example 2-1 was added, and the mixture was stirred at room temperature for 2 hours and centrifuged (3500 rpm, 5 min) to obtain approximately 950 mL of plasma having a phosphorus concentration of 0. 35 mL of the plasma having a phosphorus concentration of 10.8 mg/dL and 465 mL of the plasma having a phosphorus concentration of 0 were mixed and centrifuged (3500 rpm, 5 min) to obtain 495 mL of plasma having a phosphorus concentration of 0.8 mg/dL as a supernatant. As shown in FIG. 1, the blood purifier was assembled using the porous formed article obtained in Example 2-1. 450 mL of the obtained plasma was passed therethrough at a flow rate of 2 mL/min. 10 mL was collected for the first fraction, and 20 mL/sample was collected for subsequent fractions. Average dialysis conditions typically involve performing dialysis at flow rate Qb=200 mL/min for 4 hours. Therefore, 200 mL×4 hours=48000 mL is obtained as a total blood flow volume. When blood cell components have Ht=30%, the flow volume of plasma is 33600 mL. Since this experiment was conducted on a scale of 1/100, passing-through of 340 mL was used as a guideline. The amount of phosphorus adsorbed to the porous formed article was 1.54 mg-P/mL-Resin at the plasma flow volume of 350 mL. The low-melting point water content per 1 g dry weight of the obtained porous formed article was 0.62 g. The performance of the obtained blood purifier is shown in Table 3 below. The blood purifier had high ability to adsorb phosphorus, was free from hemolysis, and was safely usable with the number of fine particles satisfying the Approval Standards for Artificial Kidney Apparatus.

Example 2-2

217.6 g of N-methyl-2-pyrrolidone (NMP, manufactured by Mitsubishi Chemical Corp.) as the good solvent for organic polymer resins, 31.6 g of polyvinylpyrrolidone (PVP, K90 manufactured by BASF SE) as the hydrophilic polymer (water-soluble polymer), 119.2 g of lanthanum oxide (manufactured by Nacalai Tesque, Inc.) instead of MOX, and 31.6 g of polyethersulfone (PES, manufactured by Sumitomo Chemical Co., Ltd.) as the hydrophobic polymer were added, and the same operation as in Example 2-1 was performed to obtain a globular porous formed article. The particle size of the porous formed article was 533 μm. The low-melting point water content per 1 g dry weight of the PMEA-coated porous formed article was 0.14 g. The amount of phosphorus adsorbed was 9.88 mg-P/mL-Resin. The performance of the obtained blood purifier is shown in Table 3 below. The blood purifier had high ability to adsorb phosphorus, was free from hemolysis, and was safely usable with the number of fine particles satisfying the Approval Standards for Artificial Kidney Apparatus.

Example 2-3

A globular porous formed article was obtained by the same operation as in Example 2-1 except that for PMEA coating, 1.0 g of PMEA was dissolved in an aqueous solution (100 g) of 40 g of methanol/60 g of water to prepare a coating solution. Various characteristics of the obtained blood purifier are shown in Table 3 below. The low-melting point water content per 1 g dry weight of the PMEA-coated porous formed article was 1.30 g. The amount of phosphorus adsorbed was 1.55 mg-P/mL-Resin. The performance of the obtained blood purifier is shown in Table 3 below. The blood purifier had high ability to adsorb phosphorus, was free from hemolysis, and was safely usable with the number of fine particles satisfying the Approval Standards for Artificial Kidney Apparatus.

Comparative Example 2-1

A globular porous formed article was obtained by the same operation as in Example 2-2 except that PMEA coating was not performed. The performance of the obtained blood purifier is shown in Table 3 below. The low-melting point water content per 1 g dry weight of the porous formed article was 0.10 g. The results showed a low low-melting point water content, and hemolysis occurring in the porous formed article.

Comparative Example 2-2

A globular porous formed article was obtained by the same operation as in Example 2-1 except that for PMEA coating, 1.2 g of PMEA was dissolved in an aqueous solution (100 g) of 40 g of methanol/60 g of water to prepare a coating solution. The performance of the obtained blood purifier is shown in Table 3 below. The low-melting point water content per 1 g dry weight of the PMEA-coated porous formed article was 1.40 g. The amount of phosphorus adsorbed was 1.45 mg-P/mL-Resin. Too high a low-melting point water content resulted in a low amount of phosphorus adsorbed.

Comparative Example 2-3

A blood purifier was prepared in the same way as in Example 2-1 except that washing with a supercritical fluid was not performed. Various characteristics of the obtained blood purifier are shown in Table 3 below. The results showed a large number of fine particles.

TABLE 3

|  | Example 2-1 | Example 2-2 | Example 2-3 | Comparative Example 2-1 | Comparative Example 2-2 | Comparative Example 2-3 |
| --- | --- | --- | --- | --- | --- | --- |
| Hydrophobic polymer | PMMA | PES | PMMA | PES | PMMA | PMMA |
| Cytokine adsorbent | Hydrous cerium oxide | Lanthanum oxide | Hydrous cerium oxide | Lanthanum oxide | Hydrous cerium oxide | Hydrous cerium oxide |
| Hydrophilic polymer | PVP & PMEA | PVP & PMEA | PVP & PMEA | PVP | PVP & PMEA | PVP & PMEA |
| Low-melting point water content (g) | 0.62 | 0.14 | 1.30 | 0.10 | 1.40 | 0.62 |

TABLE 3-continued

|  | Example 2-1 | Example 2-2 | Example 2-3 | Comparative Example 2-1 | Comparative Example 2-2 | Comparative Example 2-3 |
|---|---|---|---|---|---|---|
| Contact-induced change rate (%) | 0.2 | 0.2 | 0 | 0.2 | 0 | 0.3 |
| Amount of platelets attached (the number (hundred million) of platelets/mL) | 3.6 | 3.6 | 3.6 | 4.1 | 3.6 | 3.6 |
| Pressure loss before blood processing (kPa) | 7.2 | 7.3 | 7.2 | 7.3 | 7.2 | 7.2 |
| Pressure loss after blood processing (kPa) | 12.0 | 12.2 | 12.0 | 13.5 | 12.0 | 12.0 |
| L/D | 1.80 | 1.80 | 1.80 | 1.80 | 1.80 | 1.80 |
| Apparent volume V of porous formed article (mL) | 350 | 350 | 350 | 350 | 350 | 350 |
| Area-average particle size (μm) | 537 | 533 | 537 | 533 | 537 | 537 |
| Cumulative pore volume at pore diameters of 5 nm or larger and 100 nm or smaller ($cm^3/g$) | 0.50 | 0.55 | 0.50 | 0.55 | 0.50 | 0.50 |
| Cumulative pore volume at pore diameters of 100 nm or larger and 200 nm or smaller ($cm^3/g$) | 0.020 | 0.021 | 0.020 | 0.021 | 0.020 | 0.020 |
| Amount of albumin adsorbed (mg/mL) | 21 | 20 | 21 | 20 | 21 | 21 |
| IL-1b adsorption rate (%) | 88 | 96 | 87 | 80 | 88 | 88 |
| IL-6 adsorption rate (%) | 67 | 77 | 65 | 58 | 66 | 67 |
| IL-8 adsorption rate (%) | 83 | 96 | 88 | 77 | 85 | 85 |
| IL-10 adsorption rate (%) | 64 | 71 | 66 | 60 | 65 | 67 |
| TNF-α adsorption rate (%) | 30 | 38 | 31 | 30 | 31 | 30 |
| HMGB1 adsorption rate (%) | 94 | 95 | 96 | 90 | 97 | 95 |
| Amount of phosphorus adsorbed from blood (mg/ml-Resin) | 1.54 | 9.88 | 1.55 | 9.87 | 1.45 | 1.55 |
| Presence or absence of hemolysis | Absent | Absent | Absent | Present | Absent | Absent |

Comparative Example 3-1

[Synthesis of Hydrophilic Polymer (Biocompatible Polymer)]

A copolymer of 2-methoxyethyl methacrylate (MEMA), N,N-diethylaminoethyl methacrylate (DEAEMA), and N-methacryloyloxyethyl-N,N-dimethylammonium-α-N-methylcarboxybetaine (CMB) was synthesized by usual solution polymerization. The polymerization conditions involved performing polymerization reaction with each monomer concentration of 1 mol/L at a reaction temperature of 60° C. for 8 hours in the presence of 0.0025 mol/L azoisobutyronitrile (AIBN) as an initiator in an ethanol solution to obtain a polymer solution. The obtained polymer solution was added dropwise to diethyl ether, and a precipitated polymer was recovered. The recovered polymer was purified by reprecipitation operation using diethyl ether. Then, the obtained polymer was dried for 24 hours under a reduced pressure condition to obtain a hydrophilic polymer (biocompatible polymer).

The molar ratio among the MEMA monomeric unit, the DEAEMA monomeric unit, and the CMB monomeric unit in the hydrophilic polymer was measured as follows: the obtained hydrophilic polymer was dissolved in dimethyl sulfoxide, followed by $^1$H-NMR measurement. From the area ratios of a peak at 4.32 ppm (derived from H atoms unique to CMB) and a peak at 2.63 ppm (derived from H atoms unique to DEAEMA), and of 0.65 to 2.15 ppm (the total amount of H atoms) in the chart thus calculated, the molar ratio was calculated according to the following expressions.

Molar ratio of the DEAEMA monomer=("Area ratio of the 2.63ppm region"/2)/("Area ratio of the 0.65-2.15ppm region"/5-"Area ratio of 2.63ppm region"×0.3)×100

Molar ratio of the CMB monomer=("Area ratio of the 4.32ppm region"/2)/("Area ratio of the 0.65-2.15ppm region"/5-"Area ratio of the 2.63ppm region"×0.3)×100

Molar ratio of the MEMA monomer=100−Molar ratio of the DEAEMA monomer−Molar ratio of the CMB monomer The molar ratio among the MEMA monomeric unit, the DEAEMA monomeric unit, and the CMB monomeric unit in the hydrophilic polymer was calculated as 80/10/10.

[Preparation of Coating Solution]

The hydrophilic polymer was added to 70 W/W % ethyl alcohol. Then, the mixture was stirred for 12 hours to prepare a coating solution having a hydrophilic polymer concentration of 0.1% by weight.

[Preparation of Polymer Beads]

A hydrophilic polymer Purosorb™ PAD950 (manufactured by Purolite Corp., acrylic polymer beads, volume-average particle size: 621 μm, cumulative pore volume at pore sizes of 5 nm to 100 nm: 0.823 $cm^3/g$, cumulative pore volume at pore sizes of 100 nm to 200 nm: 0.038 $cm^3/g$) was used. 2 mL (dry weight: 0.44 g) of the beads swollen with ultrapure water was placed in a 15 mL polypropylene (PP) conical tube. Then, 10 mL of 70 W/W % ethyl alcohol was added thereto. The tube was shaken using a shaker (In Vitro Shaker WAVE-S1, manufactured by TAITEC Corp.) with a shaking angle of 10 degrees at 40 r/min for 12 hours. Then, the solution thus shaken was filtered through a cell strainer (Mini Cell Strainer II, 70 μm nylon mesh, manufactured by Funakoshi Co., Ltd.). The absorbance at 220 nm of the solution thus filtered was measured using Shimadzu ultraviolet and visible spectrophotometer UV-2600 (manufactured by Shimadzu Corp.). Then, the beads obtained by filtration were added again to a 15 mL conical tube. This series of operations of addition of 70 W/W % ethyl alcohol to the conical tube, shaking for 12 hours using a shaker, and removal of the solution through a cell strainer was repetitively performed until the absorbance at 220 nm of the solution thus filtered reached 0.03 or lower.

[Coating Method]

To the 15 mL conical tube containing 2 mL of the polymer beads obtained by the treatment described above, 10 mL of the coating solution was added, and the tube was shaken using a shaker (In Vitro Shaker WAVE-S1, manufactured by TAITEC Corp.) with a shaking angle of 10 degrees at 40 r/min for 3 hours. Then, the solution after the coating treatment was filtered through a cell strainer (Mini Cell Strainer II, 70 μm nylon mesh, manufactured by Funakoshi Co., Ltd.) to obtain coated beads. The absorbance at 220 nm of the solution thus filtered after the coating treatment was measured using Shimadzu ultraviolet and visible spectrophotometer UV-2600. Then, the coated beads obtained by filtration were added again to a 15 mL conical tube. In this context, the amount of the hydrophilic polymer in the coating of the polymer beads (mg/dry weight g of the beads) was calculated according to the following expression. As a result, the amount of coating was 14 mg/dry weight g of the beads.

Weight (mg) of the hydrophilic polymer in the solution after the treatment=Weight (mg) of the hydrophilic polymer in the solution before the treatment×Absorbance at 220 nm of the solution after the treatment/Absorbance at 220 nm of the solution before the treatment The amount of coating (mg/dry weight g of the beads)=(Weight (mg) of the hydrophilic polymer in the solution before the treatment−Weight (mg) of the hydrophilic polymer in the solution after the treatment)/Dry weight g of the beads used Subsequently, the 15 mL conical tube containing the coated beads described above was dried in vacuum (absolute pressure: 0.003 MPa or lower) at 50° C. for 15 hours. Then, 12 mL of 20 W/W % ethyl alcohol was added into the conical tube. The tube was shaken using a shaker (In Vitro Shaker WAVE-S1, manufactured by TAITEC Corp.) with a shaking angle of 10 degrees at 40 r/min for 12 hours. Then, the solution in the impregnated beads was removed through a cell strainer (Mini Cell Strainer II, 70 μm nylon mesh, manufactured by Funakoshi Co., Ltd.), and the obtained beads were added again to a 15 mL conical tube. Then, a series of operations of addition of 12 mL of ultrapure water to the 15 mL conical tube, shaking for 3 hours using a shaker, and removal of the solution through a cell strainer was repetitively performed a total of five times. Finally, the conical tube was packed with 12 mL of saline (Otsuka Normal Saline, manufactured by Otsuka Pharmaceutical Factory) and sterilized by γ ray irradiation to obtain a porous formed article.

The low-melting point water content per 1 g dry weight of the obtained porous formed article was as low as 0.10 g, and the contact-induced change rate of the porous formed article produced unfavorable results of 0.3%. The low low-melting point water content is probably in part because the drying step was performed after coating with the hydrophilic polymer. The unfavorable contact-induced change rate is probably in part because the porous formed article before coating with the hydrophilic polymer was fragile beads and was not the hydrophobic polymer.

Comparative Example 3-2

[Preparation of Porous Formed Article]
110 g of N-methyl-2-pyrrolidone (NMP, Mitsubishi Chemical Corp.) and 150 g of a hydrous cerium oxide powder having an average particle size of 30 μm (Konan Muki Co., Ltd.) were added to a stainless ball mill pot (capacity: 1 L) packed with 1.5 kg of stainless balls having a diameter of 5 mmϕ. Milling and mixing treatment was performed at the number of rotations of 75 rpm for 150 minutes to obtain yellow slurry. To the obtained slurry, 15 g of polyethersulfone (Sumitomo Chemical Co., Ltd., Sumika Excel 5003PS (trade name), OH terminus grade, terminal hydroxy group composition: 90 (% by mol)) and 2 g of a water-soluble polymer polyethylene glycol (PEG35,000, Merck Co., Ltd.) were added, and the mixture was warmed to 60° C. in a dissolution vessel and stirred and dissolved using a stirring blade to obtain a homogeneous slurry solution for shaping.

The obtained slurry solution for shaping was warmed to 60° C. and supplied to the inside of a cylindrical rotary container in which a nozzle having a diameter of 5 mm was opened on the side. This container was rotated to form liquid droplets from the nozzle through centrifugal force (15 G). Subsequently, a polypropylene cover was put over a spatial portion between the rotary container and a coagulation vessel. The liquid droplets were allowed to travel in the spatial portion with its temperature controlled to 50° C. and relative humidity controlled to 100%, and then arrive at water as a coagulating liquid warmed to 80° C., which was retained in a coagulation vessel having an upper opening, to coagulate the slurry for shaping. Washing and classification were further performed to obtain a globular porous formed article.

[PMEA Coating of Porous Formed Article]
A cylindrical vessel (equipped with a glass filter at the bottom) was packed with 50 mL of the obtained porous formed article. Subsequently, 0.2 g of PMEA (Mn: 20,000, Mw/Mn: 2.4) was dissolved in an aqueous solution (100 g) of 40 g of ethanol/60 g of water to prepare a coating solution. The vessel packed with the porous formed article was vertically held, and the coating solution was injected from above at a flow rate of 100 mL/min so that the coating solution was contacted with the porous formed article, which was then washed with pure water. After the washing with pure water, the coating solution in the module was blown off with 0.1 KMpa of air. The module was placed in a vacuum dryer, dried in vacuum at 35° C. for 15 hours, and sterilized with gamma ray at 25 Kgy in the atmosphere.

The low-melting point water content per 1 g dry weight of the obtained porous formed article was as low as 0.01 g, and the contact-induced change rate of the porous formed article produced unfavorable results of 0.4%. This is probably because the polyethylene glycol (PEG35,000, Merck Co., Ltd.) used in the slurry solution for forming of the porous formed article was soluble in water and therefore did not remain in the porous formed article. As a result of examining the amount of PMEA in the porous formed article by ATR-IR, the amount of PMEA in the porous formed article was confirmed to be on the order of 25%.

Comparative Example 3-3

A globular porous formed article was obtained in the same way as the method described in Comparative Example 3-2 except that: the amount of NMP was changed to 147 g; the amount of the hydrous cerium oxide powder (Konan Muki Co., Ltd.) was changed to 80.5 g; the milling and mixing treatment was performed for 200 minutes; and to the obtained slurry, 21.3 g of polyethersulfone (Sumitomo Chemical Co., Ltd., Sumika Excel 5003PS (trade name), OH terminus grade, terminal hydroxy group composition: 90 (% by mol)) and 21.3 g of a water-soluble polymer polyvinylpyrrolidone (PVP, BASF Japan, Luvitec K30 Powder (trade name)) were added.

The low-melting point water content per 1 g dry weight of the obtained porous formed article was as low as 0.01 g, and the contact-induced change rate of the porous formed article produced unfavorable results of 0.4%. This is probably because the polyvinylpyrrolidone (PVP, BASF Japan, Luvitec K30 Powder (trade name)) used in the slurry solution for forming of the porous formed article was soluble in water and therefore did not remain in the porous formed article. As a result of examining the amount of PMEA in the porous formed article by ATR-IR, the amount of PMEA in the porous formed article was confirmed to be on the order of 25%.

<<Influence of Solvent in PMEA Coating Solution>>

Figure 5:
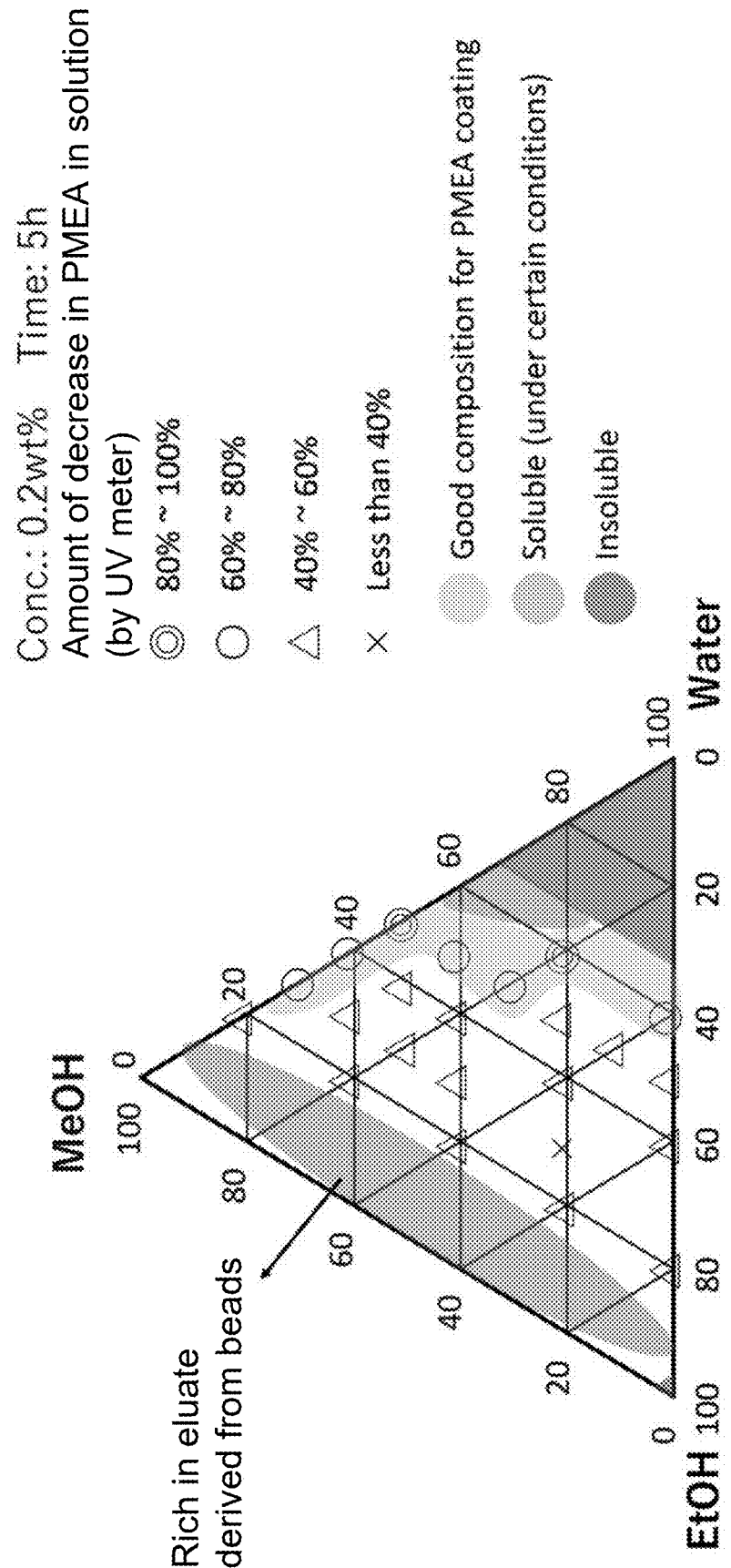
FIG. 5 is a diagram showing the PMEA solubility of a solvent in a PMEA coating solution.
Figure 6:
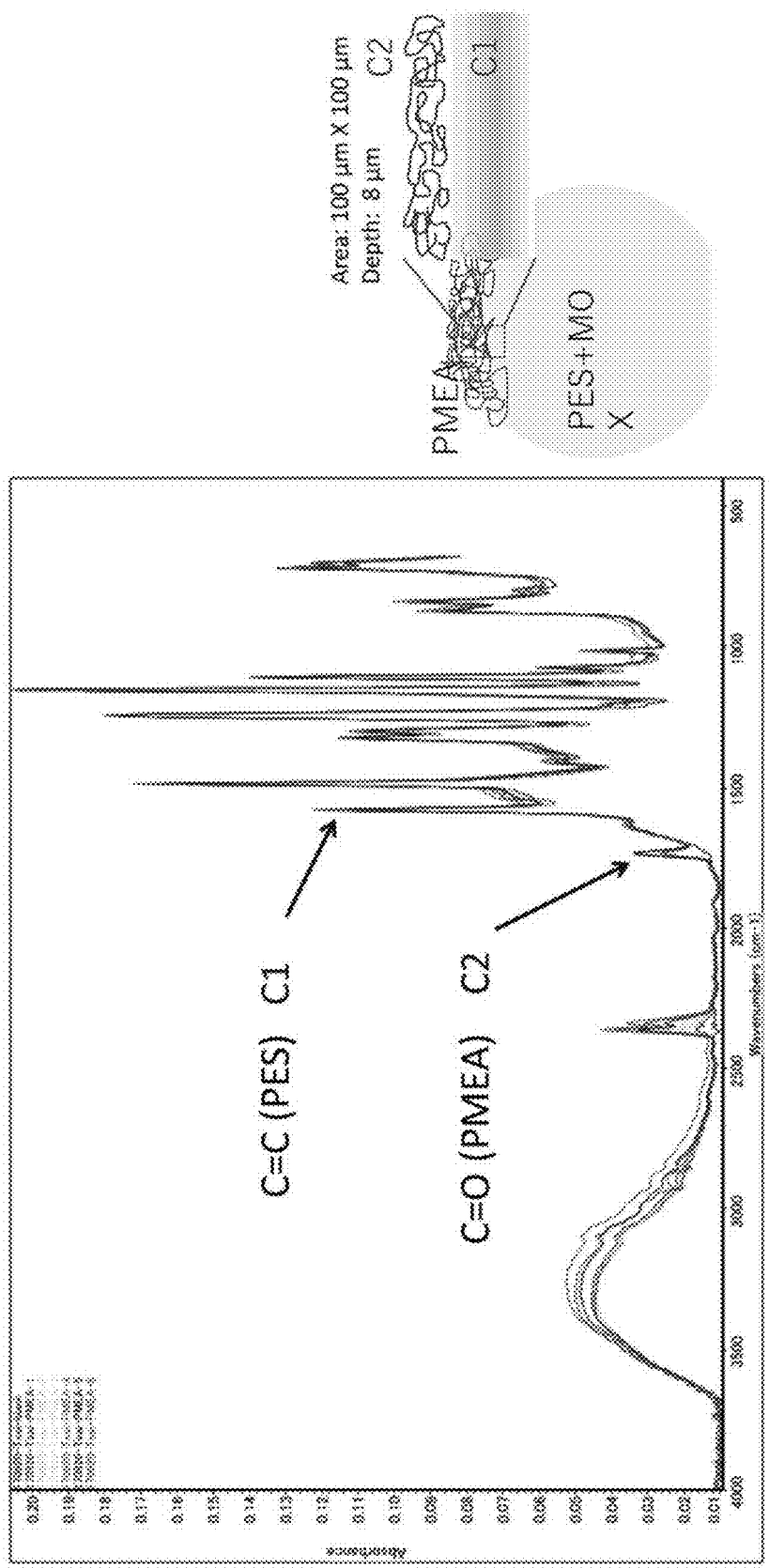
FIG. 6 shows one example of ATR/FT-IR analysis on a porous formed article comprising PES and MOX after PMEA coating.

In Comparative Examples 3-2 and 3-3 described above, an aqueous solution of 40 g of ethanol/60 g of water was used as the PMEA coating solution. By contrast, in Example 1-8 of the present application, an aqueous solution of 45 g of methanol/55 g of water was used. In Examples 2-1 to 2-3 of the present application, an aqueous solution of 40 g of methanol/60 g of water was used. FIG. 5 is a diagram showing the PMEA solubility of a solvent in the PMEA coating solution. FIG. 6 shows one example of ATR/FT-IR analysis on the porous formed article containing polyethersulfone (PES) and MOX after PMEA coating. In FIG. 6, C1 depicts a peak derived from the C=C bond of PES, and C2 depicts a peak derived from the C=O bond of PMEA. FIG. 7 shows difference in the amount of PMEA coating among solvents in the PMEA coating solution. If the same or similar PMEA concentrations are used, it is evident that the amount of coating differs drastically (about 4 times) depending on the type of the solvent used. The amount of coating by measurement using a UV meter and the C2/C1 ratio of ATR exhibited the same tendency. Hence, the methanol:water ratio as the solvent in the PMEA coating solution is preferably from 80:20 to 40:60, more preferably from 70:30 to 45:55, still more preferably from 60:40 to 45:55.

INDUSTRIAL APPLICABILITY

The blood purifier according to the present invention is excellent in blood compatibility, has favorable cytokine adsorption performance, has a low pressure loss before and after blood processing, and is safely usable. Therefore, the blood purifier according to the present invention can be suitably used in therapies for removing cytokines and HMGB1 in the body. In one embodiment, the blood purifier according to the present invention has high ability to adsorb phosphorus, is free from hemolysis, and is safely usable. Therefore, the blood purifier according to the present invention can be suitably used in therapies for regularly removing phosphorus accumulated in the body.

REFERENCE SINGS LIST

1 Thermostat bath
2 Experimental table
3 Pump
4 Column packed with porous absorbent (phosphorus absorber)
5 Pressure gauge
6 Sampling

The invention claimed is:

1. A blood purifier having a body vessel and a porous formed article placed in the body vessel, wherein:
the porous formed article comprises a hydrophobic polymer and a hydrophilic polymer, the porous formed article has a low-melting point water content of 0.12 g or larger and 2.00 g or smaller per 1 g dry weight of the porous formed article, and the porous formed article has a contact-induced change rate of 0% or more and 0.2% or less;
a ratio L/D of length L in a longitudinal direction to equivalent circle diameter D at a cross section in a shorter direction of a region occupied by the porous formed article in the body vessel is 1.00 or more and 2.30 or less, wherein the equivalent circle diameter D is calculated according to a following expression (1):

$$D = 2\sqrt{V/L/3.14} \quad (1)$$

wherein V represents an apparent volume of the region occupied by the porous formed article in the body vessel; and
the blood purifier has a pressure loss of less than 13 kPa before blood processing and the blood purifier has a pressure loss of less than 13 kPa after blood processing when an aqueous polyvinylpyrrolidone solution having a viscosity of 3.75 mPa·s or higher and 3.85 mPa·s or lower is flowed in the blood purifier at a passing rate of 400 mL/min.

2. The blood purifier according to claim 1, wherein the apparent volume V of the region occupied by the porous formed article is 210 mL or larger and 500 mL or smaller.

3. The blood purifier according to claim 1, wherein the porous formed article is in a form of globular particles.

4. The blood purifier according to claim 3, wherein the porous formed article has an area-average particle size of 300 μm or larger and 1,000 μm or smaller.

5. The blood purifier according to claim 1, wherein a cumulative pore volume at pore diameters of 5 nm or larger and 100 nm or smaller of the porous formed article is 0.5 cm³/g or more, and a cumulative pore volume at pore diameters of 100 nm or larger and 200 nm or smaller of the porous formed article is 0.2 cm³/g or less.

6. The blood purifier according to claim 1, wherein an amount of albumin adsorbed to the porous formed article is 13 mg/mL or larger and 90 mg/mL or smaller.

7. The blood purifier according to claim 1, wherein the blood purifier is configured to process whole blood.

8. The blood purifier according to claim 1, wherein the hydrophobic polymer is at least one selected from the group consisting of a styrene polymer, a polyethersulfone polymer and a polysulfone polymer.

9. The blood purifier according to claim 1, wherein the hydrophilic polymer comprises a monomer represented by a following chemical formula (1) as a monomeric unit:

[Formula 1]

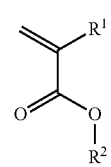

(1)

wherein $R^1$ represents a hydrogen atom or a methyl group, $R^2$ represents $-CH_2(CH_2)_qOC_tH_{2t+1}$ or $-CH_2C_mH_{2m+1}$, q represents 1 to 5, t represents 0 to 2, and m represents 0 to 17.

10. The blood purifier according to claim 1, wherein an adsorption rate for cytokines IL-1b, IL-6, IL-8 and IL-10 is 50% or more.

11. The blood purifier according to claim 1, wherein an adsorption rate for a cytokine TNF-$\alpha$ is 30% or more.

12. The blood purifier according to claim 1, wherein an adsorption rate for an alarmin HMGB-1 is 50% or more.

* * * * *

UNITED STATES PATENT AND TRADEMARK OFFICE
CERTIFICATE OF CORRECTION

PATENT NO. : 12,268,803 B2
APPLICATION NO. : 17/426841
DATED : April 8, 2025
INVENTOR(S) : T. Oishi et al.

Page 1 of 1

It is certified that error appears in the above-identified patent and that said Letters Patent is hereby corrected as shown below:

In the Claims

Column 58, Line 13 (Claim 1, Line 16) please change "D=2√V/L/3.14)" to -- D=2√(V/L/3.14) --

Signed and Sealed this
Ninth Day of September, 2025

Coke Morgan Stewart
*Acting Director of the United States Patent and Trademark Office*